(12) United States Patent  
McNeely et al.

(10) Patent No.: US 7,223,363 B2  
(45) Date of Patent: May 29, 2007

(54) METHOD AND SYSTEM FOR MICROFLUIDIC INTERFACING TO ARRAYS

(75) Inventors: Michael McNeely, Sandy, UT (US); Nils Adey, Salt Lake City, UT (US); Mark Spute, Salt Lake City, UT (US); Edward Ayliffe, Park City, UT (US); Michael Howard, Salt Lake City, UT (US); Darin Beutel, Salt Lake City, UT (US); John Jensen, Salt Lake City, UT (US); Stephen Coffin, Layton, UT (US); Thomas Moyer, Salt Lake City, UT (US)

(73) Assignee: BioMicro Systems, Inc., Salt Lake City, UT (US)

( * ) Notice: Subject to any disclaimer, the term of this patent is extended or adjusted under 35 U.S.C. 154(b) by 508 days.

(21) Appl. No.: 10/204,913

(22) PCT Filed: Mar. 8, 2002

(86) PCT No.: PCT/US02/07113

§ 371 (c)(1),  
(2), (4) Date: Aug. 26, 2002

(87) PCT Pub. No.: WO02/072264

PCT Pub. Date: Sep. 19, 2002

(65) Prior Publication Data

US 2004/0037739 A1 Feb. 26, 2004

Related U.S. Application Data

(60) Provisional application No. 60/274,389, filed on Mar. 9, 2001, provisional application No. 60/284,427, filed on Apr. 17, 2001, provisional application No. 60/313,703, filed on Aug. 20, 2001, provisional application No. 60/339,851, filed on Dec. 12, 2001.

(51) Int. Cl.  
*B01L 3/00* (2006.01)  
*G01N 31/22* (2006.01)

(52) U.S. Cl. .................... 422/58; 422/60; 422/102; 422/104; 435/286.7

(58) Field of Classification Search ............ 422/56–58, 422/60, 64–65, 102, 104; 435/286.7, 287.2  
See application file for complete search history.

(56) References Cited

U.S. PATENT DOCUMENTS 3,726,764 A 4/1973 White ..................... 195/127

(Continued)

FOREIGN PATENT DOCUMENTS

EP 0843169 5/1998

(Continued)

OTHER PUBLICATIONS

Anderson et al., "Advances in Integrated Genetic Analysis", Micro total analysis systems, Harrison and van den Berg (eds) Kluwer Academic Publishers, Dordrecht, The Netherlands, 1998, pp. 11-16.

(Continued)

*Primary Examiner*—Brian R. Gordon  
(74) *Attorney, Agent, or Firm*—Brinks Hofer Gilson & Lione

(57) ABSTRACT

A method and system for providing a fluidic interface to slides bearing microarrays of biomolecules or other samples immobilized thereon to perform a variety of chemical reactions or processing steps on the slide. An interface device seals against the slide to form a chamber or chambers containing all or a portion of the microarray, providing selective access to portions of the slide. The interface device includes inlet and outlet ports permitting liquid sample and reagents to be introduced to and removed from the chamber accessing the slide surface. Pre- and post-array microfluidic circuitry may be included in the interface device or in attachable modules. The system may include one or more compartments for collecting and storing waste fluids.

31 Claims, 17 Drawing Sheets

U.S. PATENT DOCUMENTS

| | | | | |
|---|---|---|---|---|
| 3,745,091 A | 7/1973 | McCormick | | 195/139 |
| 3,879,106 A | 4/1975 | McCormick | | 350/95 |
| 3,891,327 A | 6/1975 | Welch | | 356/244 |
| 4,171,866 A | 10/1979 | Tolles | | 350/95 |
| 4,248,904 A | 2/1981 | Fenimore | | 427/2 |
| 4,426,451 A | 1/1984 | Columbus | | |
| 4,441,793 A | 4/1984 | Elkins | | 350/536 |
| 4,447,140 A | 5/1984 | Campbell et al. | | 350/534 |
| 4,494,912 A | 1/1985 | Pauliukonis | | 417/347 |
| 4,505,557 A | 3/1985 | Golias | | 350/536 |
| 4,526,690 A | 7/1985 | Kiovsky et al. | | 210/335 |
| 4,673,657 A * | 6/1987 | Christian | | 436/501 |
| 4,687,423 A | 8/1987 | Maget et al. | | 417/379 |
| 4,722,598 A | 2/1988 | Ford | | 350/536 |
| 4,738,823 A | 4/1988 | Engelmann | | 422/56 |
| 4,790,640 A | 12/1988 | Nason | | 350/534 |
| 4,853,262 A | 8/1989 | Horie et al. | | 428/13 |
| 4,908,319 A | 3/1990 | Smyczek et al. | | 435/285 |
| 4,911,782 A | 3/1990 | Brown | | 156/633 |
| 4,948,564 A | 8/1990 | Root et al. | | 422/101 |
| 4,985,206 A | 1/1991 | Bowman et al. | | 422/99 |
| 5,023,187 A | 6/1991 | Koebler et al. | | 436/180 |
| 5,061,381 A | 10/1991 | Burd | | 210/789 |
| RE33,826 E | 2/1992 | Mitchell | | 359/398 |
| 5,100,626 A | 3/1992 | Levin | | 422/100 |
| 5,100,775 A | 3/1992 | Smyczek et al. | | 435/6 |
| 5,192,503 A | 3/1993 | McGrath et al. | | 422/57 |
| 5,200,152 A | 4/1993 | Brown | | 422/102 |
| 5,258,163 A | 11/1993 | Krause et al. | | 422/58 |
| 5,273,905 A | 12/1993 | Muller et al. | | 435/301 |
| 5,313,264 A | 5/1994 | Ivarsson et al. | | 356/73 |
| 5,346,672 A | 9/1994 | Stapleton et al. | | 422/102 |
| 5,360,741 A | 11/1994 | Hunnell | | 435/290 |
| 5,364,790 A | 11/1994 | Atwood et al. | | 435/288 |
| 5,393,494 A | 2/1995 | Greenfield et al. | | 422/68.1 |
| 5,417,576 A | 5/1995 | Hill | | 435/299 |
| 5,443,890 A | 8/1995 | Ohman | | 428/167 |
| 5,460,945 A | 10/1995 | Springer et al. | | 435/7.24 |
| 5,466,603 A | 11/1995 | Meehan et al. | | 435/285.1 |
| 5,503,803 A | 4/1996 | Brown | | 422/102 |
| 5,518,925 A | 5/1996 | Tyndorf et al. | | 435/305.2 |
| 5,527,510 A | 6/1996 | Atwood et al. | | 422/104 |
| 5,571,721 A | 11/1996 | Turner | | 435/305.1 |
| 5,578,270 A | 11/1996 | Reichler et al. | | 422/67 |
| 5,605,813 A | 2/1997 | Stevens et al. | | 435/40.52 |
| 5,637,469 A | 6/1997 | Wilding et al. | | 435/7.21 |
| 5,639,428 A | 6/1997 | Cottingham | | |
| 5,658,723 A | 8/1997 | Oberhardt | | 435/4 |
| 5,661,029 A | 8/1997 | Self et al. | | 435/288.3 |
| 5,675,700 A | 10/1997 | Atwood et al. | | 392/382 |
| 5,681,741 A | 10/1997 | Atwood et al. | | 435/287.2 |
| 5,718,567 A | 2/1998 | Rapp et al. | | 417/395 |
| 5,726,026 A | 3/1998 | Wilding et al. | | 435/7.21 |
| 5,846,727 A | 12/1998 | Soper et al. | | 435/6 |
| 5,856,174 A | 1/1999 | Lipshutz et al. | | 435/286.5 |
| 5,863,502 A * | 1/1999 | Southgate et al. | | 422/58 |
| 5,866,345 A | 2/1999 | Wilding et al. | | 435/7.21 |
| 5,876,675 A | 3/1999 | Kennedy | | 422/99 |
| 5,902,096 A | 5/1999 | Behringer et al. | | 417/395 |
| 5,922,591 A | 7/1999 | Anderson et al. | | 435/287.2 |
| 5,922,604 A | 7/1999 | Stapleton et al. | | 436/46 |
| 5,928,880 A | 7/1999 | Wilding et al. | | 435/7.21 |
| 5,935,524 A | 8/1999 | Bass et al. | | 422/104 |
| 5,948,673 A | 9/1999 | Cottingham | | |
| 5,955,028 A | 9/1999 | Chow | | 422/63 |
| 5,958,341 A | 9/1999 | Chu | | 422/99 |
| 5,958,760 A | 9/1999 | Freeman | | 435/286.5 |
| 5,989,402 A | 11/1999 | Chow et al. | | 204/601 |
| 5,989,499 A | 11/1999 | Catanzariti | | 422/63 |
| 6,008,893 A | 12/1999 | Roos et al. | | 356/246 |
| 6,020,187 A | 2/2000 | Tam | | 435/287.2 |
| 6,033,544 A | 3/2000 | Demers et al. | | 204/450 |
| 6,033,628 A | 3/2000 | Kaltenbach et al. | | 422/68.1 |
| 6,037,168 A | 3/2000 | Brown | | 435/288.3 |
| 6,043,080 A | 3/2000 | Lipshutz et al. | | 435/287.2 |
| 6,048,498 A | 4/2000 | Kennedy | | 422/99 |
| 6,052,224 A | 4/2000 | Richardson | | 359/398 |
| 6,054,277 A | 4/2000 | Furcht et al. | | 435/6 |
| 6,057,100 A | 5/2000 | Heyneker | | 435/6 |
| 6,063,579 A | 5/2000 | Bevirt | | 435/6 |
| 6,071,478 A | 6/2000 | Chow | | 422/81 |
| 6,074,725 A | 6/2000 | Kennedy | | 428/188 |
| 6,074,827 A | 6/2000 | Nelson et al. | | 435/6 |
| 6,083,763 A | 7/2000 | Balch | | 436/518 |
| 6,096,268 A * | 8/2000 | Inbar | | 422/56 |
| 6,103,199 A | 8/2000 | Bjornson et al. | | 422/100 |
| 6,114,122 A | 9/2000 | Besemer et al. | | 435/6 |
| 6,130,098 A | 10/2000 | Handique et al. | | 436/180 |
| 6,132,685 A | 10/2000 | Kercso et al. | | 422/104 |
| 6,136,592 A | 10/2000 | Leighton | | 435/288 |
| 6,140,044 A | 10/2000 | Besemer et al. | | 435/6 |
| 6,143,496 A | 11/2000 | Brown et al. | | 435/6 |
| 6,144,447 A | 11/2000 | Ohman et al. | | 356/246 |
| 6,158,712 A | 12/2000 | Craig | | 251/61.1 |
| 6,159,727 A | 12/2000 | Bochkariov | | 435/287.2 |
| 6,162,639 A | 12/2000 | Douglas | | 435/287.1 |
| 6,167,910 B1 | 1/2001 | Chow | | 137/827 |
| 6,168,948 B1 | 1/2001 | Anderson et al. | | 435/287.2 |
| 6,197,494 B1 | 3/2001 | Oberhardt | | 435/4 |
| 6,197,595 B1 | 3/2001 | Anderson et al. | | 436/180 |
| 6,200,814 B1 | 3/2001 | Malmqvist et al. | | 436/52 |
| 6,207,031 B1 | 3/2001 | Adourian et al. | | 204/451 |
| 6,225,059 B1 | 5/2001 | Ackley et al. | | 435/6 |
| 6,225,109 B1 | 5/2001 | Juncosa et al. | | 435/288.5 |
| 6,238,910 B1 | 5/2001 | Custance et al. | | 435/287.2 |
| 6,251,343 B1 | 6/2001 | Dubrow et al. | | 422/102 |
| 6,251,601 B1 | 6/2001 | Bao et al. | | 435/6 |
| 6,268,219 B1 | 7/2001 | McBride et al. | | 436/180 |
| 6,272,939 B1 | 8/2001 | Frye et al. | | 73/864.81 |
| 6,274,337 B1 | 8/2001 | Parce et al. | | 435/29 |
| 6,284,113 B1 | 9/2001 | Bjornson et al. | | 204/453 |
| 6,284,525 B1 | 9/2001 | Mathies et al. | | 435/287.2 |
| 6,284,531 B1 | 9/2001 | Zhu et al. | | 435/305.3 |
| 6,287,850 B1 | 9/2001 | Besemer et al. | | 435/287.2 |
| 6,303,288 B1 | 10/2001 | Furcht et al. | | 435/4 |
| 6,303,389 B1 | 10/2001 | Levin et al. | | 436/518 |
| 6,306,347 B1 * | 10/2001 | Mason et al. | | 422/58 |
| 6,309,875 B1 | 10/2001 | Gordon | | 435/287.2 |
| 6,326,211 B1 | 12/2001 | Anderson et al. | | 436/177 |
| 6,376,256 B1 | 4/2002 | Dunnington et al. | | 436/178 |
| 6,379,929 B1 | 4/2002 | Burns et al. | | 435/91.2 |
| 6,399,394 B1 | 6/2002 | Dahm et al. | | 436/180 |
| 6,555,361 B1 | 4/2003 | Lyman et al. | | |
| 6,569,674 B1 | 5/2003 | McGarry et al. | | |
| 6,827,906 B1 * | 12/2004 | Bjornson et al. | | 422/101 |
| 2001/0003652 A1 | 6/2001 | Freeman | | 435/286.5 |
| 2001/0018183 A1 | 8/2001 | Bao et al. | | 435/6 |
| 2001/0039057 A1 | 11/2001 | Douglas et al. | | 436/169 |
| 2002/0015667 A1 | 2/2002 | Chow | | 422/100 |
| 2002/0022261 A1 | 2/2002 | Anderson et al. | | 435/287.2 |
| 2002/0039796 A1 | 4/2002 | Dores et al. | | 436/177 |
| 2002/0071339 A1 | 6/2002 | Winkler et al. | | 366/144 |
| 2002/0074271 A1 | 6/2002 | Hu et al. | | 210/101 |
| 2002/0127146 A1* | 9/2002 | Bergh et al. | | 422/89 |
| 2002/0187560 A1* | 12/2002 | Pezzuto et al. | | 436/180 |
| 2005/0019898 A1 | 1/2005 | Adey et al. | | |

FOREIGN PATENT DOCUMENTS

| | | |
|---|---|---|
| WO | WO90/05295 | 5/1990 |
| WO | WO90/05305 | 5/1990 |
| WO | WO94/23326 | 10/1994 |
| WO | WO99/36766 | 7/1999 |
| WO | WO00/38838 | 7/2000 |

| | | |
|---|---|---|
| WO | WO00/63670 | 10/2000 |
| WO | WO01/04634 | 1/2001 |
| WO | WO01/25137 | 4/2001 |
| WO | WO01/25138 | 4/2001 |
| WO | WO01/41931 | 6/2001 |
| WO | WO01/43871 | 6/2001 |
| WO | WO01/68257 | 9/2001 |
| WO | WO01/70381 | 9/2001 |
| WO | WO01/70400 | 9/2001 |
| WO | WO01/78893 | 10/2001 |
| WO | WO01/89695 | 11/2001 |
| WO | WO01/89787 | 11/2001 |
| WO | WO01/89788 | 11/2001 |
| WO | WO01/94635 | 12/2001 |
| WO | WO02/18756 | 3/2002 |
| WO | WO02/18785 | 3/2002 |
| WO | WO02/18949 | 3/2002 |

OTHER PUBLICATIONS

Anderson et al., "Fabrication of Topologically Complex Three-Dimensional Microfluidic Systems in PDMS by Rapid Prototyping," Analytical Chemistry, vol. 72, No. 14, Jul. 15, 2000, pp. 3158-3164.

Anderson et al., "Microfluidic Biochemical Analysis System," Transducers '97 1997 International Conference on Solid-State Sensor and Acutautors, Chicago, Jun. 16-19m 1997, pp. 477-480.

Henze, Microarrays, BioForum vol. 5, Feb. 1, 2001.

Jo et al., "Fabrication of Three-Dimensional Microfluidic Systems by Stacking Molded Polydimethylsiloxane (PDMS) Layers," SPIE Conf. On Microfluidic Devices and Systems II, Sep. 1999, Santa Clara CA, SPIE vol. 3877, pp. 222-229.

Man et al., "Microfluidic Plastic Capillaries on Silicon Substrates: A New Inexpensive Technology for Bioanalysis Chips," 10th Annual IEEE MEMS Workshop, 1997, pp. 311-316.

Mitchell, Peter, "Microfluidics-Downsizing Large Scale Biology," Nature Biotechnology, vol. 19, Aug. 2001, pp. 717-721.

Unger et al., "Monolithic Microfabricated Valves and Pumps by Multilayer Soft Lithography," Science, vol. 288, Apr. 7, 2000, pp. 113-116.

Wego et al., "A self-filling micropump based on PCB technology," Sensors and Actuators A 88 (2001), pp. 220-226.

Information on Clontech Atlas™ ™ Glass Hybridization Chambers, CLONTECHniques, Jan. 2000.

Information on Corning CMT™ ™ Hybridization Chamber from Corning web site and package inserts.

Information on Grace Biolabs Hybridization Chambers from www.gracebio.com, printed Nov. 26, 2001.

Information on Schleicher and Schuell FAST™ ™ Slides, from www.s-and-s.com, printed Jan. 9, 2002.

Information on Schleicher and Schuell CAST™ ™ Slides from www.s-and-s.com, printed Jan. 9, 2002.

Information on TeleChem International, Inc., ArrayIt™ ™ Hybridization Cassette, from www.arrayit.com, printed Mar. 30, 2002.

Information on Thermo Hybaid EasiSeal, www.thermohybaid.com, printed Nov. 9, 2001.

* cited by examiner

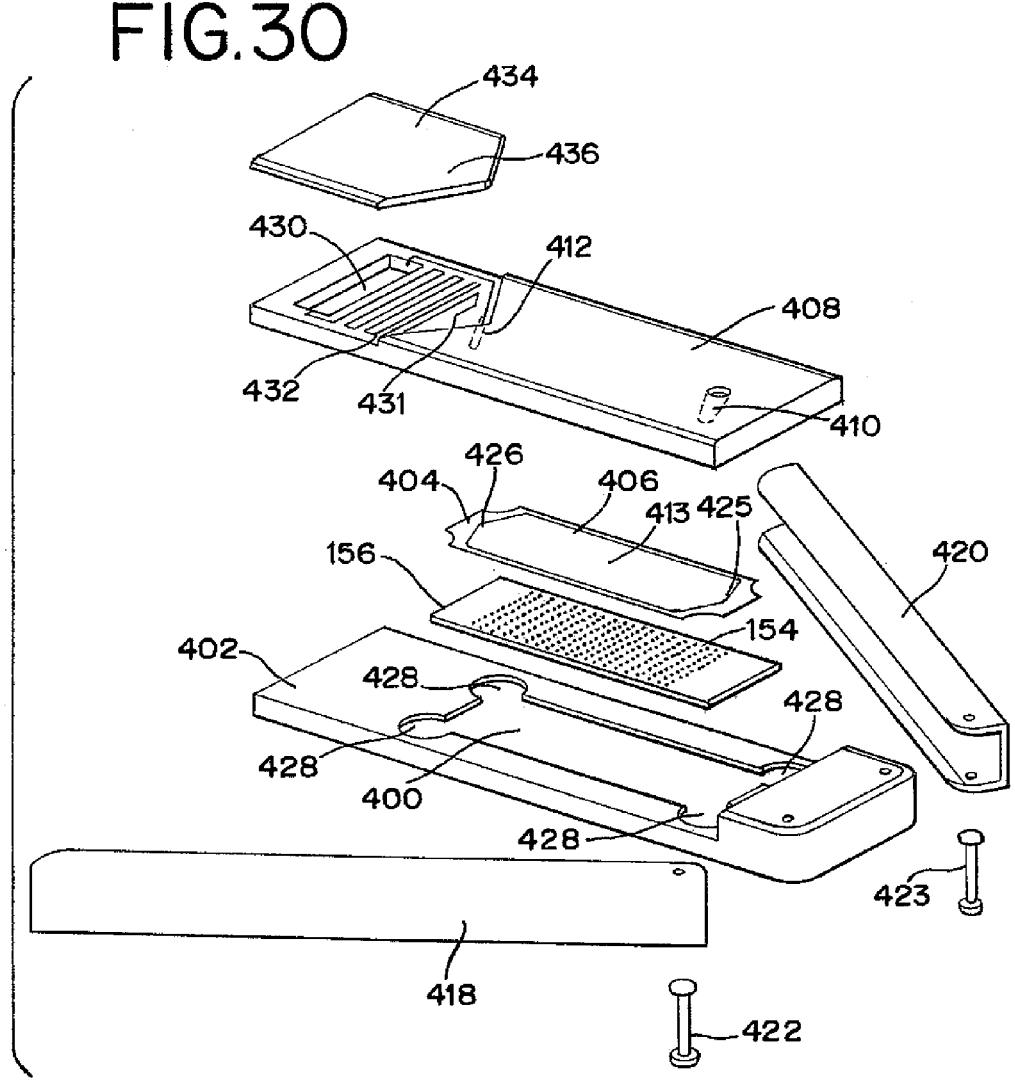

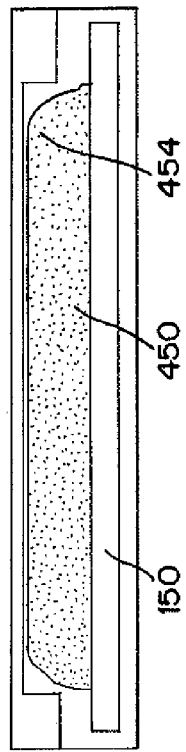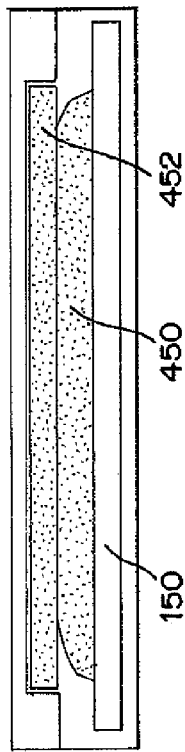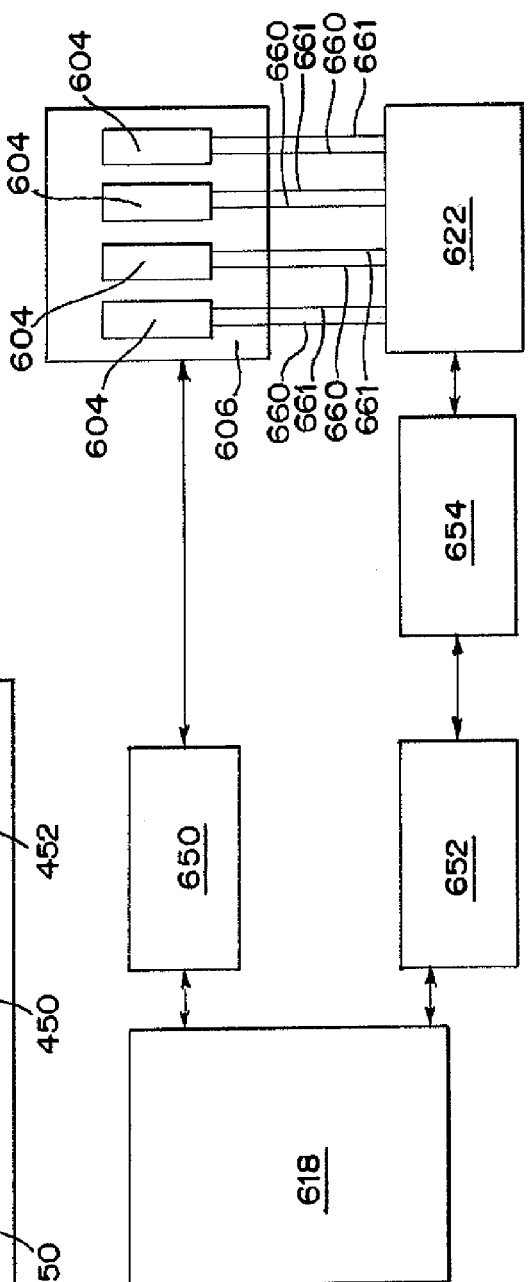

METHOD AND SYSTEM FOR MICROFLUIDIC INTERFACING TO ARRAYS

RELATED APPLICATIONS

This application claims the benefit of U.S. Provisional Application Ser. No. 60/274,389 filed Mar. 9, 2001; U.S. Provisional Application Ser. No. 60/284,427 filed Apr. 17, 2001; U.S. Provisional Application Ser. No. 60/313,703 filed Aug. 20, 2001; and U.S. Provisional Application Ser. No. 60/339,851 filed Dec. 12, 2001, which applications are incorporated herein by reference.

BACKGROUND OF THE INVENTION

1. Field of the Invention

The present invention relates generally to the field of devices for performing detection reactions involving biomolecules. In particular, the invention relates to devices for processing microarray slides used in such detection reactions. More specifically, the invention relates to a novel device for interfacing with a microarray slide to provide for the controlled delivery of fluids to selected regions of the slide surface as well as an instrument for performing simultaneous processing of a plurality of microarray slides, each used in combination with an interface device according to the invention.

2. Description of Related Art

A variety of biological and chemical assays have been developed for detecting the presence of compounds of interest in samples. In the biomedical field, methods for detecting the presence of specific nucleotide sequences, proteins or peptides are utilized, for example, in diagnosing various medical conditions, determining predisposition of patients to diseases, and performing DNA fingerprinting.

In general, biological and chemical assays are based on exposing an unknown sample to one or more known reactants and monitoring the progress or measuring the outcome of the reaction. It is often desirable to expose a sample to multiple reactants, to react multiple dilutions of a single sample with one or multiple reactants, to expose multiple samples to a single reactant, or to perform multiple repetitions of a particular assay for a given sample, in order to improve reliability. There is currently a high level of interest in the development of high throughput methods for performing multiple biological and chemical analyses of this type simultaneously, quickly, and conveniently.

One recently developed method for performing multiple chemical reactions simultaneously is to form a microarray of multiple spots of reactant molecules on a planar substrate such as a glass microscope slide, typically in a two-dimensional grid pattern, and apply liquid reagents and reactants to the slide to contact multiple spots simultaneously. Various reaction steps may be preformed with the bound molecules in the microarray, including exposure of bound reactant molecules to liquid reagents or reactants, washing, and incubation steps. The progress or outcome of the reaction (or other association between bound molecules and reagents which is not truly a reaction) may be monitored at each spot in the microarray in order to characterize either material(s) immobilized on the slide or material(s) in a liquid sample. Although it is typical to immobilize known reactants on the substrate and expose an unknown liquid sample (e.g., a "probe solution") to the immobilized reactants and monitor the reaction between the sample and the various reactants in order to characterize the sample, it is also possible to immobilize one or more unknown samples on the substrate and expose them to a liquid containing one or more known reactants.

Microarrays are frequently used in analysis of DNA samples, but may also be used in diagnostic testing of other types of patient samples. Spots in microarrays may be formed of various large biomolecules, such as DNA, RNA, and proteins, smaller molecules such as drugs, co-factors, signaling molecules, peptides or oligonucleotides. Cultured cells may also be grown onto microarrays. As an example, if it is desired to detect the presence of particular DNA sequences in a patient sample, the sample is exposed to a microarray of spots formed of oligonucleotides having sequences complementary to sequences of interest. If the DNA sequence of interest is present in a patient sample, it will hybridize with the bound oligonucleotides. The occurrence of hybridization at a particular spot then indicates the presence of the sequence associated with that spot in the sample. Hybridization can be detected by various methods, many of which give indication of the quantity, as well as presence, of sequences of interest in the sample. One commonly used method involves labeling the sample with a fluorescent dye so that fluorescence can be detected at spots where hybridization occurred. Various types of slide readers are commercially available for reading microarray slides.

Microarrays offer great potential for performing complex analyses of samples by carrying out multiple detection reactions simultaneously. However, a current limitation of microarrays is the time and care required to process slides to obtain reliably high quality results. The need for high quality processing is particularly pronounced because individual microarrays slides are expensive and only limited quantities of the samples used in the reactions may be available, making it particularly important to obtain good results consistently.

Both manual and automated methods of processing microarrays have been developed. However, to date, no method has been completely satisfactory. In order to process a microarray manually, at certain reaction steps the appropriate reagent or reactant solution is applied to the microarray slide and a cover slip applied to spread the solution out into a thin layer that covers the entire microarray and prevents evaporation. Washing steps are typically carried out by placing slides in jars of wash solution. Each processing step must be carried out by hand, necessitating a large amount of human effort. Moreover, the success of the procedure is largely dependent on the skill of the human technician. A single technician is typically able to process at most only 10-15 slides per day. An additional drawback of manual processing techniques is that an essentially open system is used, presenting a high potential for evaporation, spilling or leakage of samples or reagents. If microarray slides are allowed to dry out, data quality will be compromised. Leakage and spilling can be a significant problem, in that certain samples or reagents may be hazardous, and also because leakage or spilling of genetic material, even in minute amounts, can contaminate other samples being processed in the lab and lead to erroneous results.

Various methods have been developed to overcome the limitations of manual slide processing. These range from simple slide processing chambers designed to simplify the application of solutions to microarray slides and reduce evaporation and leakage of solutions, to large and expensive machines capable of processing large numbers of slides simultaneously.

Loeffler et al. (PCT publication WO 00/63670, dated Oct. 26, 2000 describe a slide processing chamber designed for processing microarray slides. Freeman (U.S. Pat. No. 5,958, 760, issued Sep. 28, 1999 Stapleton et al. (U.S. Pat. No. 5,922,604 issued Jul. 13, 1999 Stevens et al. (U.S. Pat. No. 5,605,813, issued Feb. 25, 1997 and Richardson (U.S. Pat. No. 6,052,224, issued Apr. 18, 2000 all disclose slide processing chambers not specifically disclosed for use in microarray processing, but which serve to illustrate the general state of the art relating to the processing of individual slides.

Devices capable of processing multiple slides simultaneously in an automated fashion are described by Custance (U.S. Pat. No. 6,238,910, issued May 29, 2001 and Juncosa et al. (U.S. Pat. No. 6,225,109, issued May 1, 2001).

All of the above mentioned patents or applications are incorporated herein by reference.

Devices for automated processing of microarray slides offer many advantages, but are prohibitively expensive for labs that do not need to process large numbers of slides. In addition, even with improved reproducibility delivered by automation, the results obtained with commercially available instruments of this type frequently do not meet the high quality and consistency standards that are desirable, particularly because of the cost of microarray slides and the often limited availability of samples.

With increased interest and development effort in the field of microarrays, equipment used to manufacture microarrays on slides has been developed which allows for the formation of arrays with higher spot densities and smaller individual spot sizes. At the same time, detection equipment used with microarrays is becoming capable of detecting smaller spots at higher densities. However, some tests are best performed with a number of spots less than the total number that can be formed on a slide. It would be desirable to exploit the higher spot density and higher density detection capability by performing several such tests simultaneously on a single slide, essentially breaking one large high density array into a number of smaller arrays. It would thus be advantageous to have a method of interfacing to a microarray which would permit selective access to portions of a microarray.

There remains a need for a method of interfacing to microarray slides which eliminates or minimizes leakage or spillage, provides reliable, reproducible results, requires minimal volumes of samples and reagents, and can be used conveniently for manual processing of small numbers of slides but may also be adapted to automated slide processing for handling larger numbers of slides.

SUMMARY OF THE INVENTION

The present invention is a system for processing microarray slides that is made up of a microarray interface device and an instrument capable of holding a plurality of microarray slides, interfacing with the microarray slides via their associated interface devices, and controlling various reaction conditions during processing of the microarray slides. The novel microarray interface device can be connected to a substrate bearing a microarray of spots made up of DNA, RNA, oligonucleotides, proteins, or other biomolecules. In particular, the array interface device is adapted for interfacing with glass microscope slides and similar planar substrates. The interface device provides for the delivery of sample, reagents, rinses, and so forth, to selected portions of the array in a controlled manner. In an alternative embodiment of the invention, the selective access to the array substrate provided by the interface device may be used in the formation of the spot microarray on the substrate. Although the device has been designed particularly for interfacing with slides bearing microarrays, the device may also be used to provide a fluid interface to slides bearing various other types of samples, and the application of the device is not limited to use with microarray slides.

The interface device seals against the surface of the microarray substrate. A sealing layer or gasket positioned between the interface device and substrate provides a uniform, non-leaking seal between the interface device and substrate. A clamp mechanism may be used to secure the interface device and substrate together. Indentations or grooves in surface of the interface device are aligned with spots in the microarray, so that when the interface device is sealed to the microarray substrate, the indentations or grooves form one or more reaction chambers, chambers or channels containing spots in the microarray. Alternatively, interface channels, chambers, or wells may simply be defined by openings in a sealing or gasket layer. Interface channels, chambers, or wells may access individual spots, groupings of spots, e.g. rows or blocks of spots within the array, or all spots in the array. Size and configuration of interface channels or wells are selected to provide uniform filling with minimal bubble formation. Interface channel volumes are kept low to reduce the amounts of sample and reagents that must be used.

The interface device includes one or more inlets and one or more outlets, which communicate with the interface channels, chambers or wells and which allow fluids to flow into and out of the interface channels, chambers or wells to contact the spots contained therein. The invention may be provided with inlet and outlets suitable for manual introduction and removal of fluids via pipette or syringe, for example, or automated introduction and removal of fluids from the device via tubing connected to a device such as a pump device.

The interface device may include pre-array fluidic circuitry between the inlets to the interface device and the interface channels, chambers, or wells, and post-array circuitry between the outlets of the interface channels, chambers or wells and the outlets of the interface device. Microfluidic circuitry may also be provided in series between several interface channels, chambers, or wells. Fluidic circuitry may include various microfluidic circuit elements, such as valves, reservoirs, structures for mixing or dividing fluid streams, stop junctions, air inlets, and air vents, which may be used to perform various fluid control, handling or processing steps with liquid reagents or reactants. Alternatively, or in addition, pre- or post-array processing may be provided in one or more separate modules connected to the interface device. Reactants may be present in the microfluidic circuitry within the interface device or in pre-processing or post-processing modules so that reaction or processing steps may be performed in these structures as well as on the microarray slide itself. As an example, the array interface and pre- or post-processing modules may be configured to perform labeling, pre-hybridization, and hybridization steps used in the processing of microarray slides.

The interface device has the capability to collect and store waste fluids subsequent to their passing through the device. In a preferred embodiment of the device, waste fluids are contained in a disposable portion of the interface device.

The interface device may include electrodes or other sensors for monitoring the movement of fluids within the system and the progress of reactions occurring therein. Electrodes may also be included within the device for producing electrokinetic movement of molecules in solution within the device. Heating elements or mixing mechanisms may be included in some embodiments of the interface device.

The interface device may be constructed by microfabrication or other techniques similar to those used in the integrated circuit and microelectromechanical systems (MEMS) and microfluidic systems industries, which are effective for fabricating micrometer sized structures for manipulating small volumes of fluids.

In a preferred embodiment of the invention, the interface device and slide are placed in a base that supports and stabilizes the slide and interface device, controls various parameters of slide processing, and may perform a number of auxiliary functions. In the most preferred embodiment of the invention, the base is a part of an instrument that may handle the processing of multiple slides simultaneously. The mechanism for clamping together the slide and the interface device may be incorporated into the base. The base may include a humidity chamber that surrounds the exterior of the seal between the slide and interface device. Heating or cooling elements may be provided in the base or in the instrument to allow reactions to be carried out at various temperatures. The base or instrument may include a mechanism for mixing or agitating of fluids within the interface channels and possibly other portions of the interface device to enhance chemical reactions. In certain embodiments of the invention, the instrument is capable of receiving and securing multiple slides for simultaneous processing in an automated slide processing system. The instrument may include a microprocessor, memory, and other electronics for controlling heating, cooling, mixing, and other functions carried out by the inventive device. In certain embodiments of the invention, the base is formed separately from an external control module that controls heating or mixing functions performed by the base.

It is an object of the invention to provide controlled delivery of fluids to one or more selected regions of a microarray slide. This is accomplished by appropriate choice of size and shape of interface channels or wells. By delivering fluids selectively to several different regions of the microarray, it is possible for multiple reactions to be carried out simultaneously, for parallel processing of multiple different samples or multiple repetitions of a single sample.

It is an object of the invention to provide a method and system for processing microarray slides using very small volumes of samples and reagents at all processing steps. This is achieved by including microfluidic pre and post-processing circuitry in the interface device and attached modules to allow all processing steps to be performed with microvolumes of fluids. Minimal use of reagents and sample is cost effective and makes the system useful in cases where limited amounts of sample are available.

It is a further object or the invention to provide a method and system for processing microarrays which provides mixing of fluids on the microarray surface, while at the same time requiring only small volumes of sample and reagents. This is accomplished by using a reaction chamber having flexible wall portions that are moved by a novel pneumatic mixing system.

It is an object of the invention to provide a device for filling an interface chamber on a microarray slide evenly and without bubble formation. This is accomplished by appropriate selection of chamber size and configuration. Even, bubble-free filling results in more controlled delivery of reactants and reagents to the microarray and consequently better results from the processed microarray.

It is an object of the invention to provide an interface device that seals reversibly to a microarray slide without leaking or sample loss. Reversible, leak-free sealing is obtained through the use of appropriately selected gasket or O-ring material between the interface device and slide. A good seal provides for more successful processing of the microarray and minimizes problems associated with contamination of lab space by leaked reagents and reactants.

It is an object of the invention to provide a microarray interface device for interfacing with microarray slides that allows for performance of pre- and post-processing steps. This is accomplished by providing microfluidic circuitry in the interface device, and, depending on the processing steps required, additional pre- or post processing modules attached in fluid communication with the interface device. By providing for all stages of processing to be performed with the use of the inventive interface device, convenience and efficiency of slide processing is greatly enhanced.

It is an object of the invention to provide for the capture and containment of waste fluids resulting from microarray processing. This is achieved by providing a waste reservoir within the interface device connected to the outlet(s) of the interface channels or wells. By storing waste in the interface device, the collection and disposal of waste is greatly simplified and the safety and convenience of microarray processing is improved.

It is an object of the invention to provide a system for performing manual processing of individual microarray slides in a reliable and reproducible fashion. This is accomplished through the use of an interface device that receives manually delivered reagents and reactants and provides them to the surface of a microarray slide in a controlled manner.

It is an object of the invention to provide a system for processing multiple microarray slides simultaneously in an automated fashion. This object is achieved by multiplexing the microarray slide processing system to accommodate a desired number of slides.

BRIEF DESCRIPTION OF THE DRAWINGS

FIG. 30 is a exploded perspective view of an alternative embodiment of the invention;

FIG. 33 is a cross sectional view of an interface channel containing a liquid filler;

FIG. 34 is a cross sectional view of an interface channel containing a solidified filler;

FIG. 35 is a block diagram of an instrument for controlling processing of a microarray slide;

DETAILED DESCRIPTION OF THE INVENTION

Figure 1:
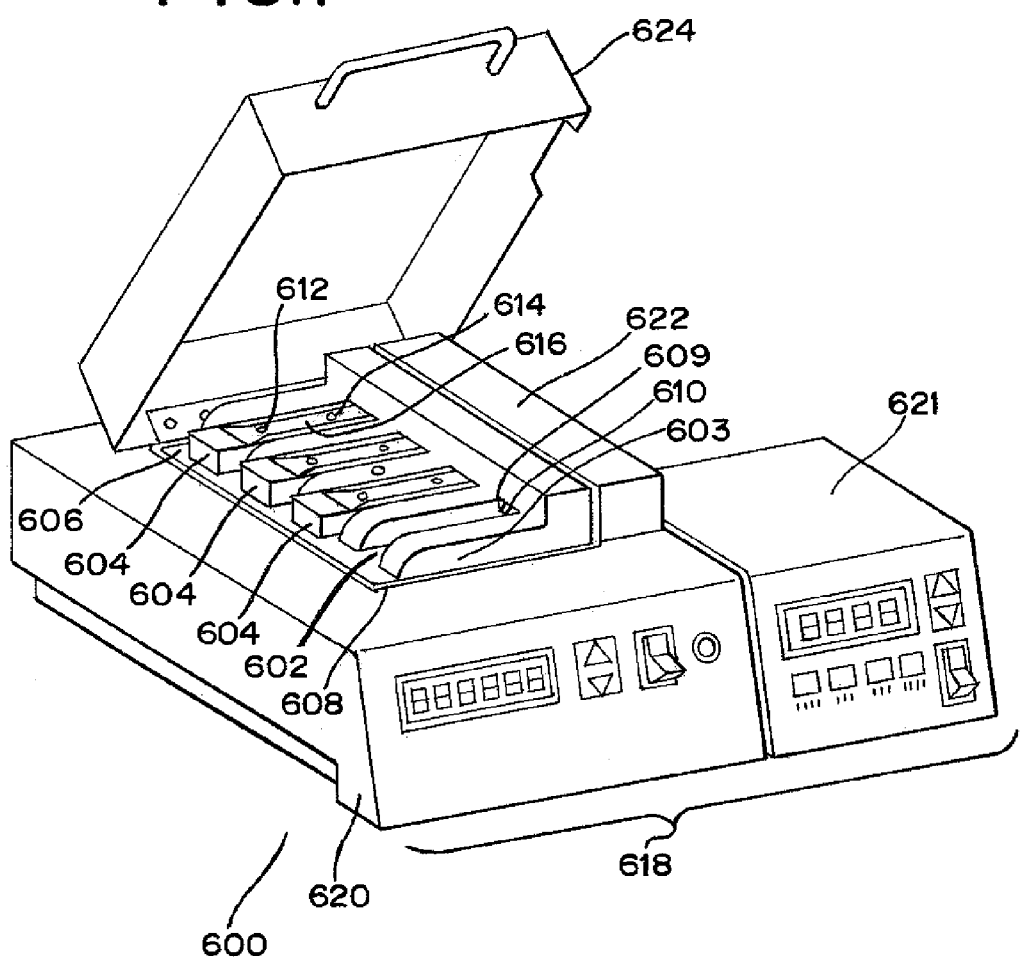
FIG. 1 is a perspective view of an exemplary embodiment of a slide processing device manufactured according to the invention.

FIG. 1 depicts an example of a presently preferred embodiment of the invention. The invention includes an instrument 600, which includes multiple bays 602, each of which is adapted to receive a reaction device 604, which is made up of a microarray slide in combination with a microarray interface device. Bays 602 are located in base 603 on heat block 606, which fits into well 608 in instrument 600. Base 603 is formed as a part of heat block 606, or is formed separately and mounted on heat block 606. In either case, base 603 and bays 602 are in thermal communication with heat block 606. Reaction devices 604 are heated by heat block 606 during microarray processing. Each reaction device 604 mates with air connectors 609 and 610, visible in the empty bay 602. Air line connectors 609 and 610 are connected to a pressure source in instrument 600, which is used to drive mixing of fluid in reaction device 604. In the embodiment of the invention depicted in FIG. 1, sample, reagent, and wash liquids are introduced into each reaction device via inlet hole 612, while air or liquid exits reaction device via outlet hole 614. Inlet hole 612 and outlet hole 614 are formed in interface device 616 and are in fluid communication with a reaction chamber on the surface of the microarray slide. Control panel 618 allows the user to control the various functions performed by instrument 600, e.g. heat block temperature and mixing parameters. In this particular example, instrument 600 is made up of a commercial laboratory heater 620 of the type used for heating test tubes, Eppendorf tubes, and the like, and a pump unit 621, so that the pump unit 621 and heat block 606 portion of the device can be manufactured separately from laboratory heater 620. Pump unit 621 pumps air alternately into and out of air line connectors 609 and 610 of each reaction device 604 via manifold 622. The same functions could be provided by an instrument in which pump and heating units were built in the same instrument case. Instrument 600 may include an opaque lid 624 to keep the microarray slides from being exposed to light, since light may bleach out dyes commonly used during microarray processing. Lid 624 may also provide thermal insulation.

Figure 2:
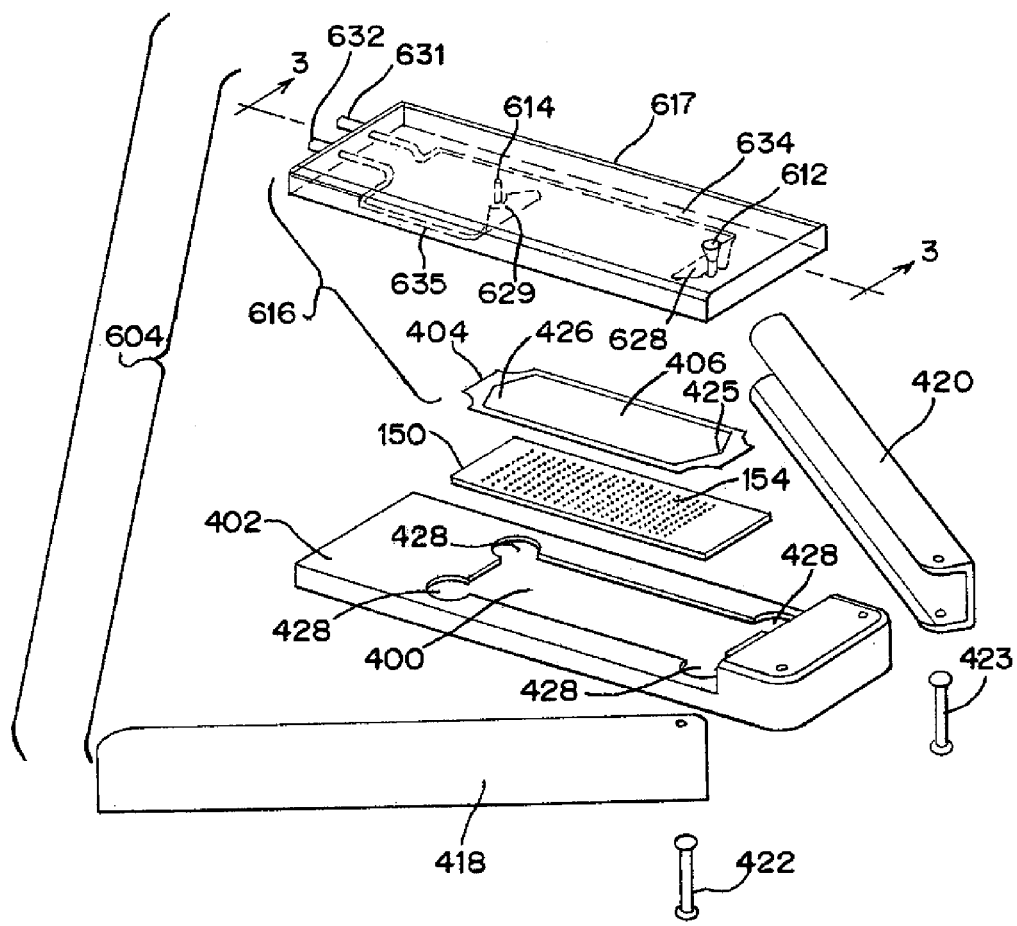
FIG. 2 is a perspective view of a microarray slide/interface device combination.

FIG. 2 is an exploded view of reaction device 604. As described in connection with FIG. 1, reaction device 604 includes interface device 616 sealed to microarray slide 150. In this case, interface device 616 is made up of main interface layer 617 and gasket 404. A reaction chamber is formed between the upper surface of slide 150 and the lower surface of main interface layer 617, the boundaries of the reaction chamber being defined by opening 406 in gasket 404. Fluids are injected into the reaction chamber via inlet 612. As fluids are injected, air or fluid already present in the reaction chamber may escape via outlet 614. The reaction chamber allows interaction of fluids with substances spotted onto slide 150 in microarray 154. Air bladders 628 and 629 are formed in the interior of main interface layer 617, and joined to connectors 631 and 632 via air channels 634 and 635, respectively. Connectors 631 and 632 allow reaction device 604 to mate with air line connectors 609 and 610 of instrument 600. The lower surfaces of air bladders 628 and 629 are thin and flexible, so that they are deflected downward or upward as the pressure in air bladders 628 and 629 either increased or increased. The lower surface of main interface layer 617 can be formed of a membrane of a thin, flexible material, attached to a more rigid material which forms the bulk of main interface layer 617, or the lower surface may be formed of the same material as the remainder of main interface layer 617, with the flexibility imparted by the thinness of the material. In this case, in order to form open structures in the interior of main interface layer 617, main interface layer 617 can be formed in one or more layers that are attached together by various standard manufacturing methods. Interface device 616 and slide 150 are clamped together by placing slide 150 into recess 400 in base 102, placing interface device 616 (which includes gasket 404 attached to the underside thereof) over slide 150, and clamping everything together with a clamp mechanism such as C-channel clamps 418 and 420, which pivot inward on pins 422 and 423.

Figure 3:
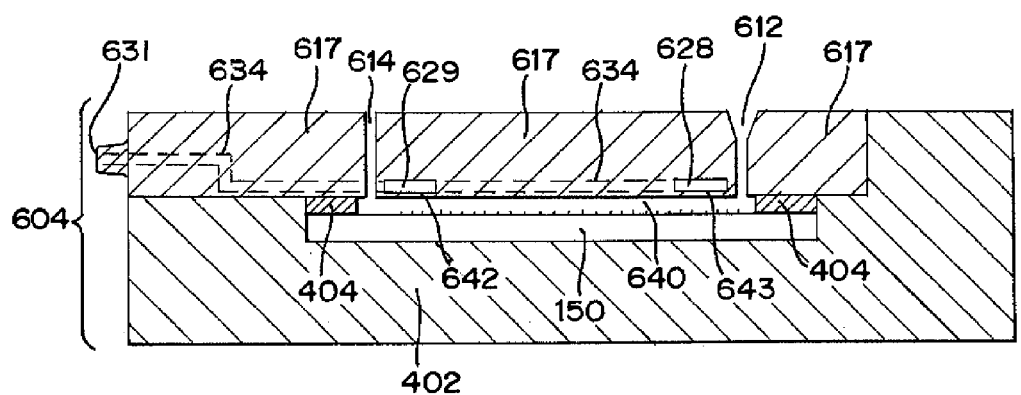
FIG. 3 is a cross-sectional view of the microarray slide/interface device combination of FIG. 2.

FIG. 3 shows a cross section of the reaction device 604. Gasket 404 seals main interface layer 617 to microarray slide 150 to form reaction chamber 640. Fluid enters reaction chamber 640 via inlet 612, and as it enters, air escapes via outlet 614. Air bladders 628 and 629 are located over either end of reaction chamber 640, but do not communicate directly with reaction chamber 640. In order to agitate the fluid in reaction chamber 640, one bladder (e.g. bladder 628) will be pressurized to cause the lower surface 643 to be deflected downward into reaction chamber 640, while the other (e.g. bladder 629) will be depressurized to cause lower surface 642 to deflect upward. By alternately inflating and deflating the two bladders, in reciprocal fashion, fluid movement sufficient to cause mixing can be generated in reaction chamber 640. Positive and negative pressure is provided to bladder 628 via air channel 634, and bladder 629 via air channel 635 (not shown). The height of reaction chamber 640 is defined by the thickness of gasket 404. In the preferred embodiment of the invention, gasket 404 has a thickness of at least about 15 µm and at most about 300 µm, more preferably between about 20 µm and about 30 µm, more preferably about 23 µm to about 27 µm, and most preferably about 25 µm. As gasket thickness is decreased, roughness of the slide surface and lower surface of the interface device, and nonuniformity of the gasket may become problematic. Moreover, if the gasket thickness is decreased further, the chamber may become too difficult to fill. Therefore, while it is desirable to have a small reaction chamber volume, it appears that reducing the volume by reducing the chamber height causes problems if the height goes below about a certain height. The chamber volume can be reduced by changing the size of opening 406 in gasket 404. If opening 406 in gasket 404 is large enough to fit around the largest microarray typically formed by commercial spotting equipment, a reaction chamber volume of at most about 36 µl to about 54 µl, more preferably about 41 µl to about 49 µl, and most preferably about 45 µl will be obtained. Providing that it is acceptable for reaction chamber 640 to contain a smaller microarray (or partial microarray), opening 406 can be made considerably smaller, with an associated reduction in chamber volume.

FIGS. 2 and 3 depict an interface device which forms a single reaction chamber on the surface of a microarray slide. However, reaction chambers, channels, and wells having various configurations can be formed on microarray slides according to the present invention. The following examples illustrate more clearly the important aspects of reaction chambers, channels, and wells formed by interface devices.

Figure 4:
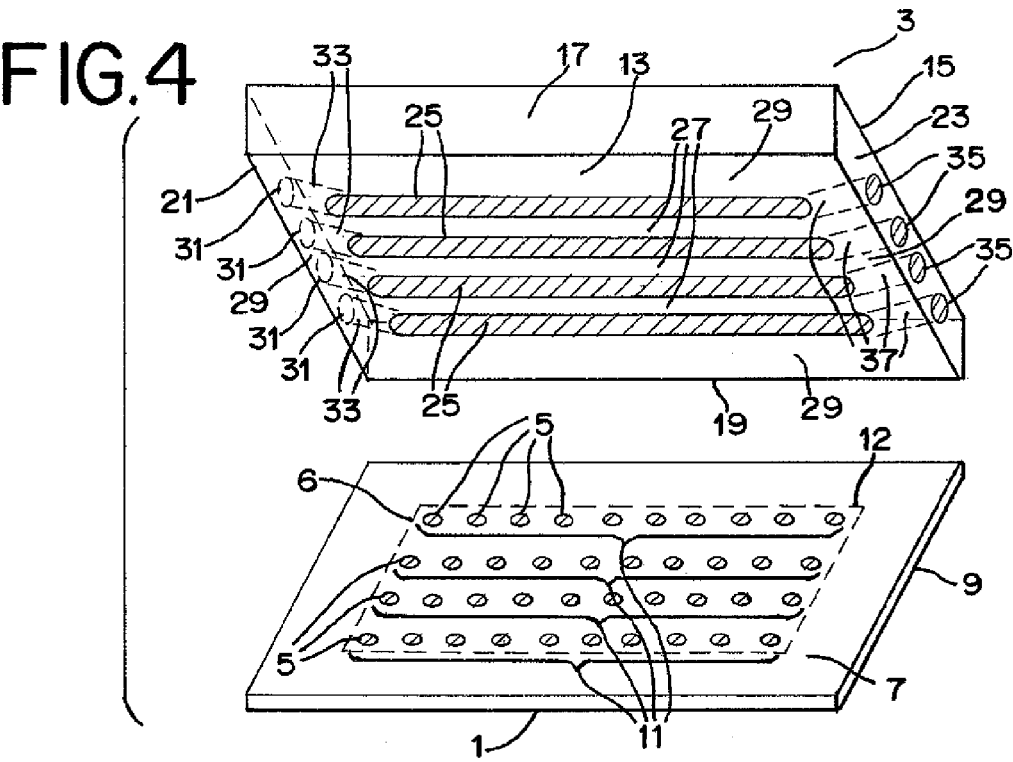
FIG. 4 is a perspective view of a microarray of spots formed on a planar substrate and an embodiment of an interface device constructed according to the present invention.

FIG. 4 depicts a microarray slide 1 and interface device 3 prior to sealing of the two together. Microarray slide 1 includes a plurality of spots 5 arranged in a spot array 6 on surface 7 of planar substrate 9. Spots 5 are formed of biomolecules or other reactant materials immobilized on surface 7. Planar substrate 9 is commonly a glass microscope slide, but substrates formed of other materials and having other dimensions may be used as well. The invention is not limited to any particular substrate; however, it is necessary that the interface device can be sealed against the surface of whatever substrate is used. Spot array 6 can be formed by various methods, including pin spotting, ink jet technology, or by selective growth of molecules on the substrate.

The spots in exemplary spot array 6, as shown in FIG. 4, are arranged in regularly spaced columns 11 and rows 12. In this example, for simplicity, four columns 11, each containing ten spots, are used. In practice, microarrays typically contain much larger numbers of spots, but the invention is not limited to any particular number of spots, nor is it limited to any particular arrangements of spots. Array patterns are used because the row and column arrangement makes it easy and convenient to reference specific spots, but the invention may be used to interface with arrays or other patterns of spots containing anywhere from a single spot to very large numbers of spots, limited only by the size of the substrate and the minimum spacing required for visualization of individual spots during detection or monitoring steps. Moreover, interface device 3 may also be used with a substrate 9 on which biomolecules or reactants are not localized into spots, but may be arranged in other groupings or distributed substantially uniformly over surface 7 of substrate 9.

Figure 25:
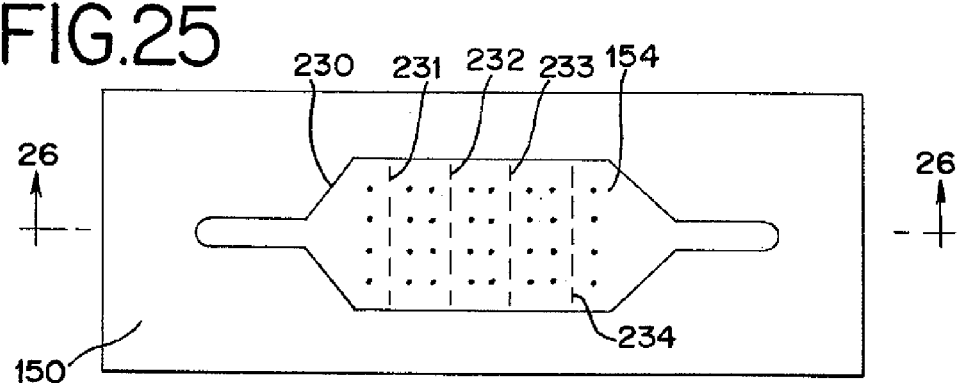
FIG. 25 depicts an interface channel configuration for accessing an entire microarray on a microarray slide.
Figure 26:
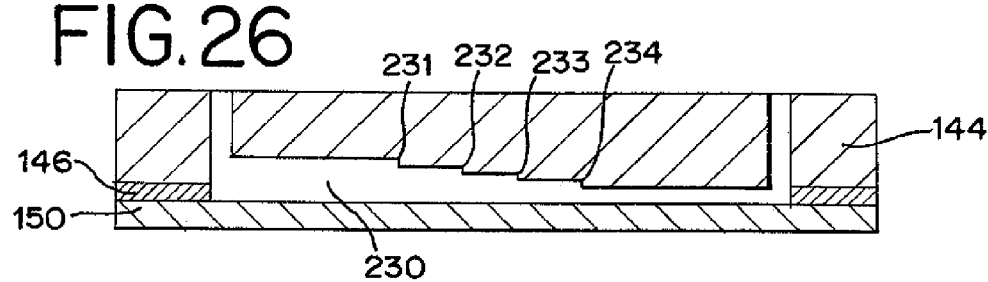
FIG. 26 is a cross section of an interface channel designed to reduce formation of bubbles during fluid introduction.
Figure 27:
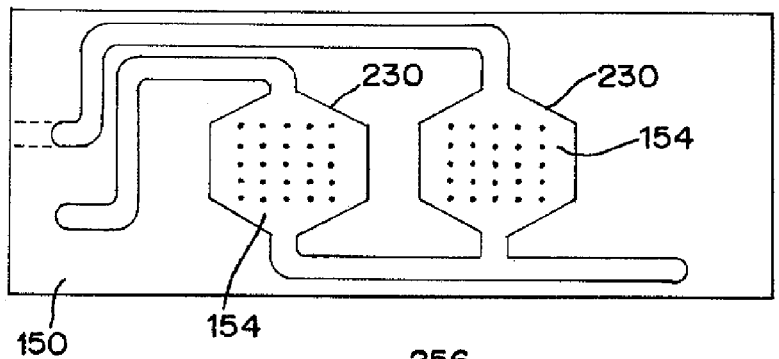
FIG. 27 depicts an interface channel configuration for accessing multiple microarrays on a microarray slide.

In certain applications, it may be desirable to use the interface device to access one or more complete spot microarrays on a microarray slide. As shown in FIGS. 25 and 27, arrays 154 of spots on the microarray slide 150 are accessed by one or a few whole-array reaction chambers 230 formed at the interface of microarray slide 150 and the main interface layer 144. The shape and height of the reaction chamber 230 may be defined by gasket 146, or the reaction chamber may extend into the bottom surface of the main interface layer as well. In order to minimize the formation of bubbles as fluid is introduced to the reaction chamber, it may be desirable for the reaction chamber to have a stepped cross section, as shown in FIG. 26. Smooth, uniform, filling of the reaction chamber, without bubble formation, is provided by utilizing an reaction chamber 230 that is relatively narrow at the fluid inlet and widens gradually outward to the fill width of reaction chamber 230. Similarly, reaction chamber 230 narrows gradually at the outlet. If hydrophobic materials are used for microarray slide 150 and main interface layer 144, and fluid is introduced through the inlet at the larger end of reaction chamber 230, the fluid will tend to spread out to fill the entire area between the inlet and line 231, before entering the slightly shallower region of reaction chamber 230 between lines 231 and 232. Similarly, the region between lines 231 and 232 will tend to fill before the still shallower region between lines 232 and 233. This will reduce uneven filling patterns that may lead to bubble formation. If a hydrophilic material is used, the same stepped reaction chamber configuration may be used, but fluid should be introduced at the shallower end of the reaction chamber, because with hydrophilic materials, the shallower region will fill first, due to stronger capillary forces. A gradually sloping, rather than stepped, reaction chamber profile would function in substantially the same manner.

Another example of an interface device for accessing a large portion of a microarray slide is shown in FIG. 30. In this embodiment of the invention, microarray slide 150 is set into recess 400 in base 402, gasket 404 is preferably positioned on microarray slide 150 so that opening 406 forms a reaction chamber 413 containing microarray 154, and interface device 408 is positioned over gasket 404 so that inlet channel 410 and outlet channel 412 communicate with reaction chamber 413 formed between interface device 408 and microarray slide 150 and bounded by opening 406 in gasket 404. Pivoting c-channel clamp members 418 and 420, which are pivotally mounted on base 402 by pins 422 and 423 swing inward to slide onto the edges of the "sandwich" formed by base 402, microarray slide 150, gasket 404 and interface device 408. Clamp members 422 and 423 are linear sections of c-channel, which may be formed of metal, plastic, or other rigid materials. If an appropriately selected gasket material is used, good sealing of microarray slide 150, gasket 404, and interface device 408 can be obtained without a large amount of pressure. We have found that effective sealing is obtained with gaskets formed of flexible thermoplastic film composed of butadiene, low molecular weight polyethylene and paraffin wax, and sold under the name Parafilm M™ by the American Can Company. Another suitable alternative gasket material is MJ Film™, a wax sheet material sold by MJ Research, Inc., Waltham, Mass. These materials undergo deformation that is primarily plastic, rather than elastic, when compressed. Once the gasket has deformed (compressed) due to the pressure applied by clamp members 418 and 420, the system of microarray slide 150, gasket 404 and interface device 408 is sealed and held together but no longer under significant pressure. Gasket 404 may also be formed of elastic materials, such as silicone rubber, or may be formed as a separate component or applied directly to the underside of interface device 408, by silk-screening, printing, etc.

As discussed previously in connection with the embodiment of the invention shown in FIGS. 25-27, the reaction chamber is narrow at inlet end 425 and outlet end 426, and angles outward gradually to its full width to provide for smooth, bubble-free filling and emptying. The amount of compression of gasket 404 may be controlled by stops or shims (not shown) having a known thickness formed in the surface of base 402 or interface device 408 adjacent gasket 404 by machining, or by application of a thin layer of material by silk-screening or other methods. By forming shims or stops at a specified thickness, the height (and thus the volume) of reaction chamber 413 can be controlled.

In the example depicted in FIG. 30, recess 400 of base 402 includes finger enlargements 428 at its corners to permit easy placement and removal of microarray slide 150. Waste reservoir 430 is provided on the upper surface of interface device 408. Serpentine seal 432 permits the escape of air, but not fluid. Waste reservoir 430 and serpentine seal 432 are covered by cap 434, which may be sealed to interface device 408 by various methods (epoxy, heat sealing, etc.). Air vent 436 in cap 434 communicates with the end 431 of serpentine seal 432 to permit the escape of air. Various alternative structures could be used to allow air such as, for example, a hydrophobic membrane or a capillary tube. The device of FIG. 30 may be used as an independent device, to provide a low volume reaction chamber for convenient delivery of fluids to the microarray slide surface, and need not be used in connection with an instrument, as shown in FIG. 1. It does not include air bladders to provide pneumatic mixing.

In an alternative embodiment of the invention, recess 400 may be configured as a humidity chamber, through the inclusion of a gasket, O-ring, or other sealing means to form a water-tight seal between base 402 and interface device 408. By adding a suitable fluid to recess 400 before base 402 and interface device 408 are sealed together (with microarray slide 150 positioned in recess 400), a humid environment can be created around the seal between microarray slide 150 and interface device 408 to prevent the evaporation of fluid from reaction chamber 413.

Base 402 may also include structures for providing heating and mixing functions during microarray processing.

In some cases, it may be desirable to use the novel interface device to selectively access certain portions of a microarray slide. FIG. 4 illustrates an embodiment of the invention which allows fluids to be delivered to individual columns 11 of a microarray. In FIG. 4, interface device 3 has an interface surface 13 adapted to fit against surface 7 of microarray slide 1, a top surface 15, sides 17 and 19, and ends 21 and 23. Interface surface 13 includes parallel grooves 25 corresponding to columns 11 of spot array 6, which are separated by dividing walls 27 and bordered by outer walls 29. Grooves 25 are connected to interface inlets 31 by inlet channels 33 and to interface outlets 35 by outlet channels 37.

Figure 5:
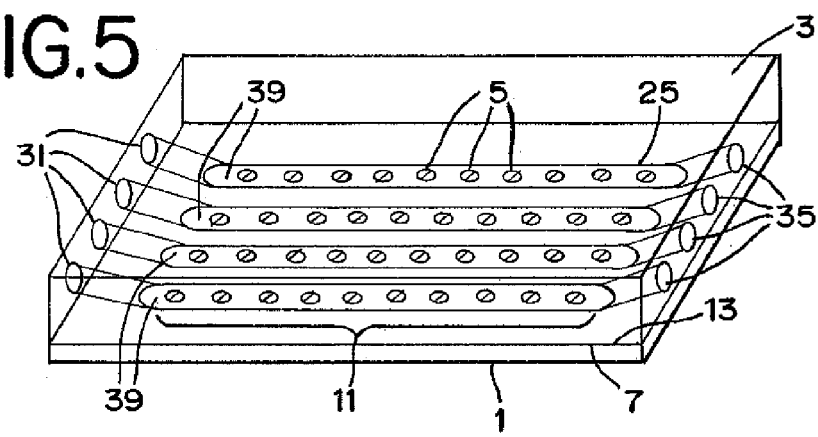
FIG. 5 is a perspective view of the interface device and microarray substrate of FIG. 4 sealed together.

As shown in FIG. 5, when interface surface 13 is pressed against surface 7 of microarray slide 1, grooves 25 are closed or covered by surface 7 to form closed interface channels 39. In this embodiment of the invention, each interface channel 39 contains a column 11 of spots 5. Interface inlets 31 and interface outlets 35 in interface device 3 provide access to interface channels 39.

Figure 6:
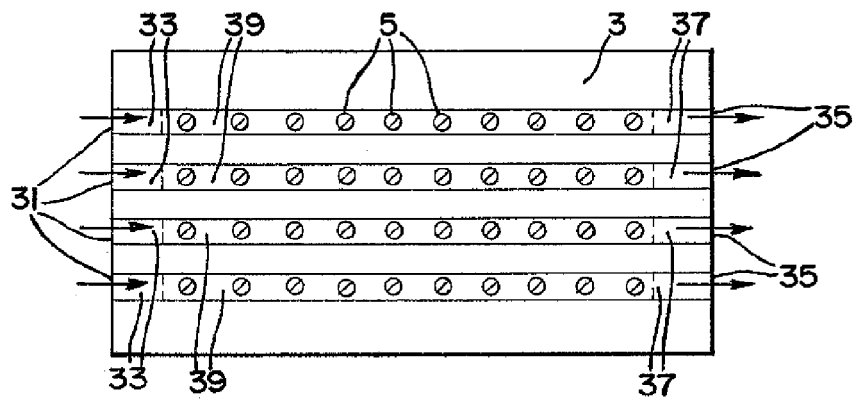
FIG. 6 is a top view of the microarray substrate and interface device as shown in FIG. 5.

FIG. 6 shows a top view of interface device 3, including spots 5 on microarray slide 1, interface channels 39, inlet channels 33, outlet channels 37, interface inlets 31, and interface outlets 35. In this example, fluid samples may enter interface inlets 31, travel through interface channels 39 and over spots 5, and exit the interface device interface through outlets 35.

Figure 7:
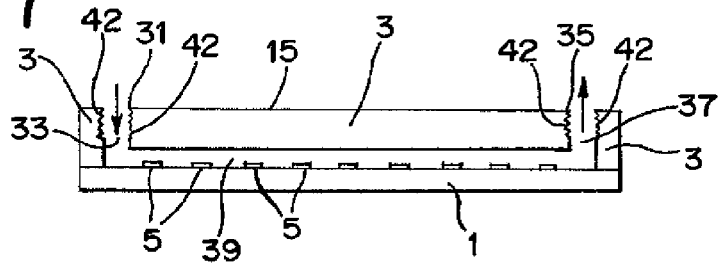
FIG. 7 depicts an alternative method of forming inlets and outlets in an interface device.
Figure 8:
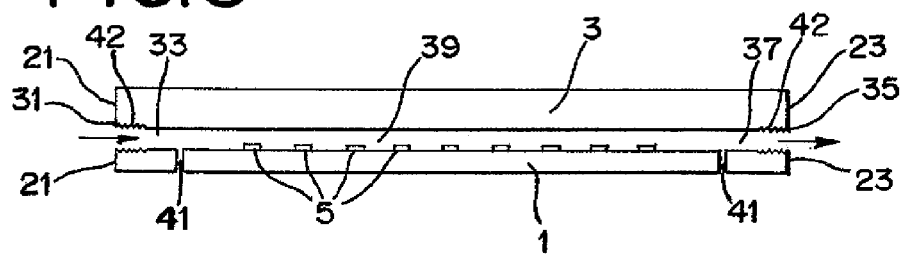
FIG. 8 depicts another alternative method of forming inlets and outlets in an interface device.

The embodiment of the invention shown in FIGS. 4-6 permits columns 11 of spots 5 to be accessed individually. Continuous flow of samples, reagents, or other reactants may be provided to each column of spots. Inlet channels 33 and outlet channels 37 may be closed channels formed in the interior of interface device 3, as shown in these figures. It would also be possible to form inlet channels 33 and outlet channels 37 as open grooves in interface surface 13 of interface device 3, continuous with grooves 25, which would similarly form closed channels when interface device 3 was sealed to microarray slide 1. Two alternative methods of forming inlet channels 33 and outlet channels 37 are shown in FIGS. 7 and 8. In the embodiment shown in FIG. 7, inlet channels 33 and outlet channels 37 are formed perpendicular to interface channel 39, and interface inlets 31 and interface outlets 35 are in top surface 15 of interface device 3. In the embodiment of FIG. 8, a recess 41 is formed in interface device 3, sized to receive micro array slide 1. Inlet channels 33 and outlet channels 37 are formed parallel and continuous with interface channel 39, and interface inlets 31 and interface outlet 35 are in the ends of interface device 3. Interface inlets 31 and interface outlets 35 may include threads 42 for connection to external tubing, as shown in FIGS. 7 and 8, or other types of connectors as are well known to those of ordinary skill in the art. Interface inlet 31 and interface outlets 35 may be threaded, or include other types of connectors in the other embodiment of the invention, as well.

Figure 9:
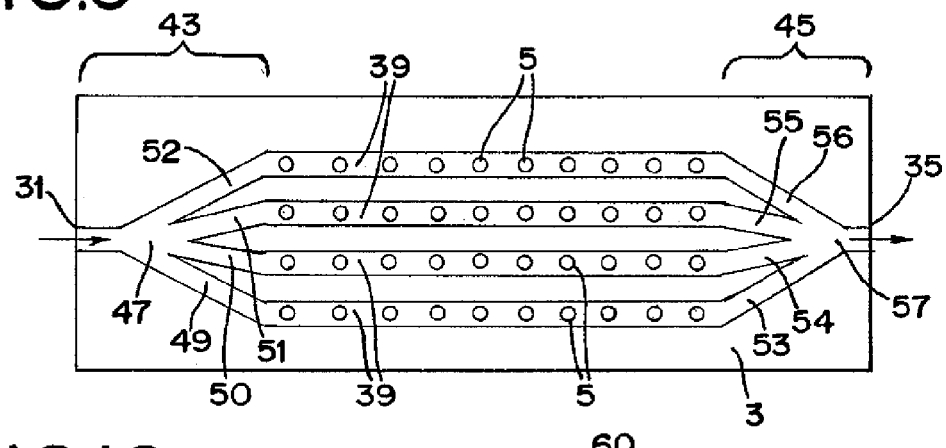
FIG. 9 is a top view of an embodiment of the interface device, showing the microarray, including pre- and post-array microfluidics.

FIG. 9 depicts an alternative two-dimensional embodiment of the invention in which pre-array microfluidic circuitry 43 is included between interface inlet 31 and interface channel 39, and post-array microfluidic circuitry 45 is included between interface channel 39 and interface outlets 35. In this example, pre-array microfluidic circuitry 43 includes branching point 47 which divides fluid entering via a single interface inlet 31 into four prearray channels 49, 50, 51 and 52, which are delivered to individual interface channels 39. Post-array microfluidic circuitry 45 receives the outputs of multiple interface channels 39 via four post array channels 53, 54, 55, and 56, and combines them at junction point 57 to form a single output stream which exits interface device 3 via a single interface outlet 35.

In the example shown in FIG. 9, pre-array microfluidic circuitry 43 performs the simple task of dividing a single fluid stream into multiple fluid streams, while post-array microfluidic circuitry 45 adds multiple fluid streams to form a single fluid stream. However, pre-and post-array microfluidic circuitry may perform more complex processing using microfluidic methods and structures as are known in the art or as may be developed subsequently. Pre- and post-array microfluidic circuits may have any number of inlets and outlets, as required by the particular application.

Figure 10:
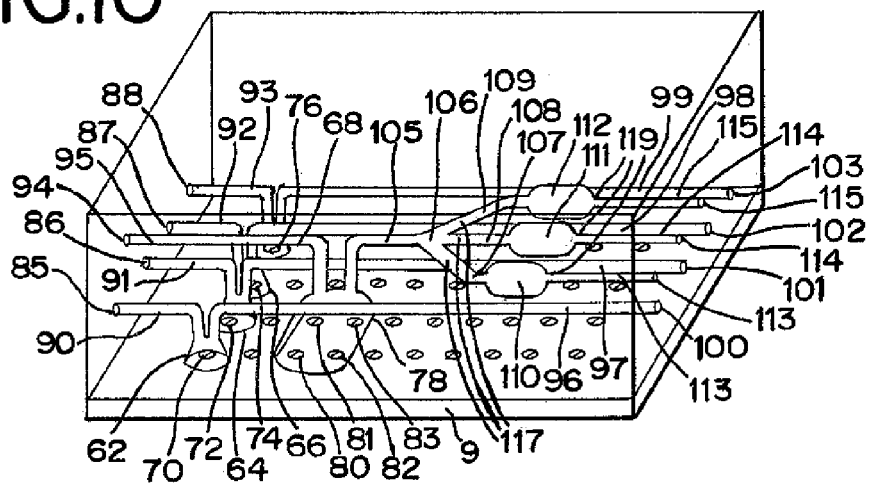
FIG. 10 is a perspective view of a three-dimensional interface device sealed to a microarray substrate.

A three-dimensional embodiment of the invention, which may be used to selectively access individual spots or groups of spots in a microarray, is shown in FIG. 10. Multiple individual spots or multiple discrete groups of spots (other than those in a columnar arrangement or a limited number of other arrangements) cannot readily accessed with a substantially planar or "two-dimensional" interface device as shown in FIGS. 1-9, because inlet and outlet channels and microfluidic circuitry would overlap. By moving inlet and outlet channels to different planes or levels of the interface device structure, more selective access to different spots can be obtained. 3D interface device 60 includes reaction chambers 62, 64, 66 and 68, which provides access to a single spots 70, 72, 74 and 76 on substrate 9, and reaction chamber 78, which provides access to a group of spots 80, 81, 82, and 83 on microarray slide 1. Interface inlets 85, 86, 87 and 88 allow fluid to be introduced to reaction chambers 62, 64, 66 and 68, respectively, via channels 90, 91, 92 and 93. Interface inlet 94 allows fluid to be provided to reaction chamber 78, via channel 95. Channels 96, 97, 98 and 99 carry fluid from reaction chambers 62, 64, 66 and 68 to interface outlets 100, 101, 102 and 103, respectively. Thus, each of spots 70, 72, 74 and 76 can be accessed individually by a single fluid stream with direct flowthrough. In contrast, channel 105 from reaction chamber 78 leads to a post-array microfluidic circuit made up of branching point 106, which diverts the fluid stream from channel 105 into three branches 107, 108 and 109 leading to reservoirs 110, 111, and 112, and air escape channels 113, 114, and 115, which provide for the escape of air or other gas from reservoirs 110, 111 and 112, via interface outlets 113, 114 and 115. Valves 117 at branching point 116 control the flow of fluid into branches 107, 108 and 109, and stop junctions 119 at the outlets of reservoirs 110, 111, and 112 prevent the flow of fluid, but not air, out of the reservoirs. This post-array microfluidic circuitry is representative of the type of circuitry used in processing of DNA.

The 3D interface device 60 depicted in FIG. 10 illustrates a number of important features of the invention. It shows that it is possible to interface with multiple individual dots or with non-columnar groups of dots. It also illustrates that both a larger number of channels connecting interface inlets, well, and interface outlets may be included in a 3D structure than in a 2D, or planar structure, and that micronuidic circuitry (either or both pre- and post-array) may be included in the interface device, and positioned over the array if desired. By including a sufficient number of layers in the 3D structure, it would be possible to access every spot in the microarray individually, if desired, or to include a variety of microfluidic circuitry in the interface device.

The inventive interface device makes it possible to incorporate individual spots or groups of spots in a microarray into one or more microfluidic circuits. This allows the use of various microfluidic methods in the processing of the spots. The examples presented in FIGS. 1-10 include several examples of microfluidic circuitry. However, the inventive interface device may include other types of microfluidic circuitry as desired for processing of spots on the microarray, and the invention is not limited to the microfluidic circuitry shown herein. The types of microfluidic circuit components that may be formed in the interface device include, but are not limited to branches, junctions, valves, stop junctions, and reservoirs. Microfluidic circuitry may include structures for mixing or dividing of fluid streams and starting and stopping the flow of fluid into and out of specific channels, wells, or reservoirs.

Fluids may be moved into and through microfluidic circuits by a number of methods, including electrokinetics, electro-hydrodynamics, and applied pressure. The most appropriate choice will depend on the flow rates involved, whether or not the solution is ionic, and the type of materials used for the microarray substrate and the interface device. Passive control of fluids within microfluidic circuits is also possible, by taking advantage of capillarity caused by the attraction or repulsion of a fluid toward certain materials. Commonly owned U.S. Pat. No. 6,296,020, issued Oct. 2, 2001 discloses a number of microfluidic circuit structures based on hydrophobic passive valving that are suitable for use in the present invention. However, other types of microfluidic circuit components may be used, as well, and the invention is not limited to any particular type of microfluidic circuitry.

Various types of valves can be included in pre- and post-array microfluidic circuitry, including mechanical valves, and passive valves such as hydrophobic fluid channel narrowings and capillary valves. Remote valving, which controls fluid flow by using external valves to control the venting of air in specific regions of the circuit, thus modulating backpressure that opposes fluid movement, may also be used. A method and system for remote valving is disclosed in commonly owned PCT International Patent Publication No. WO 02/12734, which is incorporated herein by reference.

Air escape channels and stopping means may be included in the fluid circuitry. In most utilizations of pressure driven flow, the microfluidic circuit is open to the atmosphere at one or more points downstream of the moving fluid so that air displaced by the moving fluid is allowed to escape the circuit. This prevents unwanted buildup of pressure that may oppose the desired fluid movement. The fluid may be prevented from escaping the circuit through the air displacement ducts by use of capillary valves, porous hydrophobic membranes, or similar methods, where air may escape but the fluid is contained. As noted above, modulating the escape of air can be used to control movement of fluid within the circuit.

Interface devices according to the present invention, are preferably formed from materials such as glass, silicon, or certain plastics, such as PTFE, FEP, PFA, PET, PMAA or PC. Two-dimensional and three-dimensional microfluidic circuitry of the interface device can be formed by various techniques, including micro-lithography, chemical etching, thin film deposition, hot embossing, micro-injection molding, or laser machining using both IR and UV lasers.

Channels, wells, reservoirs, valves, and other components of microfluidic circuitry can generally be easily formed in a surface of a piece of material used to construct the interface device, but are less readily formed in the interior of a solid piece of material. Therefore, in order to form circuit components located within the interface device, and to form multi-layer (3D) structures, the interface device may be formed in multiple layers. For example, an open channel (groove) or well is formed in a first layer, and a second layer is sealed or secured to the first layer to form a top surface which closes the channel or well. Individual layers are aligned and sealed to form a three dimensional, multi-layer structure. The sealing method is dependent on the materials that are to be joined, but may include eutectic or anodic bonding, the use of adhesives or epoxies, or ultrasonic welding. In cases in which a straight channel penetrates into the interior of the interface device from an exterior surface (e.g., channels 31 and 35 in FIGS. 4, 7 or 8), the channel can be formed by machining or etching from the exterior of the interface device.

Some fluid control techniques require electronic access to a part of the fluidic circuit. For example, both electro-kinetic and electro-hydrodynamic fluid control utilize electrodes that are attached to flow channels and valves within a fluid circuit. In some cases it may be desirable to include heating elements within the interface device structure. Mechanical valves or pumps, or heating elements all require electrical interfacing. If these control elements are embedded within a multi-layer system, then electrical traces may have to be brought to the outside of the interface device to connect to control circuitry. All such additional components are considered to be within the scope of the invention.

Although the interface device may be formed of either hydrophobic or hydrophilic materials, in many cases it is advantageous to utilize a hydrophobic material for some or all of the device. Hydrophilic materials generate capillary forces which are inversely proportional to the size of the feature. Thus, small gaps in hydrophilic multi-layer structures can generate huge capillary forces, causing hydrophilic capillary systems to be generally unstable. Structures formed of hydrophobic materials and using hydrophobic capillary valves allow better control of fluid flow, because aqueous fluids are not drawn into hydrophobic channels, but must be driven in under pressure. In addition, the interface surface of the interface device must be fit closely to and seal with the surface of the microarray substrate. If the interface device is formed from a hydrophobic material, or has a hydrophobic surface coating, leakage of aqueous solutions between the interface device and substrate will be minimized. Suitable hydrophobic materials include PTFE, FEP and PFA. The interface device may also be constructed from a non-hydrophobic material, such as silicon, glass, PET, PMMA, or PC, and, if desired, hydrophobic coatings can be formed on hydrophilic materials by vacuum deposition techniques, spin coating, or vapor deposition of hydrophobic materials.

Gaskets used to provide sealing between the interface device and microarray slide may be formed of a resilient material such as silicone, closed-cell foam, or rubber, or of a less resilient material coated with a resilient material, e.g. silicone-coated PTFE or other plastic. We have found that another suitable gasket material is a flexible, thermoplastic film composed of butadiene, low molecular weight polyethylene and paraffin wax, and sold under the name Parafilm™ by the American Can Company, Chicago, Ill. Yet another suitable gasket material is MJ Film™, a wax sheet material sold by MJ Research, Inc., Walthaim, Mass. These materials are primarily plastic rather than elastic. Other sealing structures which may be used include O-rings of elastic or plastic materials, or layers of sealant materials applied or formed directly on the interface device or the slide. Sealing of the interface device to the microarray slide may also be accomplished with the use of an adhesive "gasket" layer, in which case it may not be necessary to clamp the slide and interface device together to achieve sealing. However, in some cases it may be effective to provide both clamping and an adhesive layer, with the clamping functioning to increase the strength of the bond provided by the adhesive.

The interface device may be manufactured in such a way that some or all of it can be disposable. In the case of multi-layer devices, it may be desirable to make certain layers disposable, and others non-disposable. In particular, it is advantageous for layers that contact sample and reagent materials to be disposable, while layers that contain active elements (electrodes, heating elements, and the like) or other expensive-to-manufacture components, are preferably reusable. Naturally, it must also be possible to manufacture the device in such a way that after use the device can be separated into disposable and reusable portions.

Figure 11:
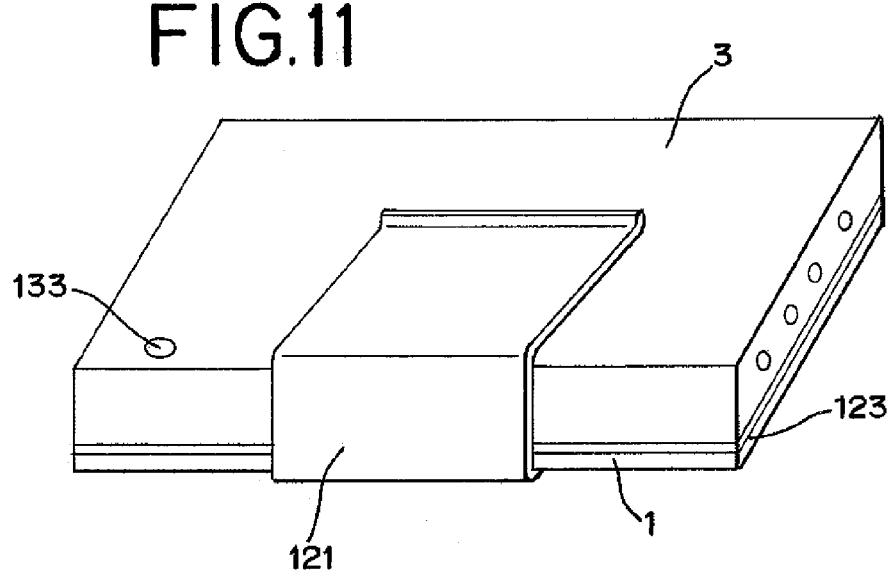
FIG. 11 illustrates a method of clamping the interface device to a microarray substrate.
Figure 12:
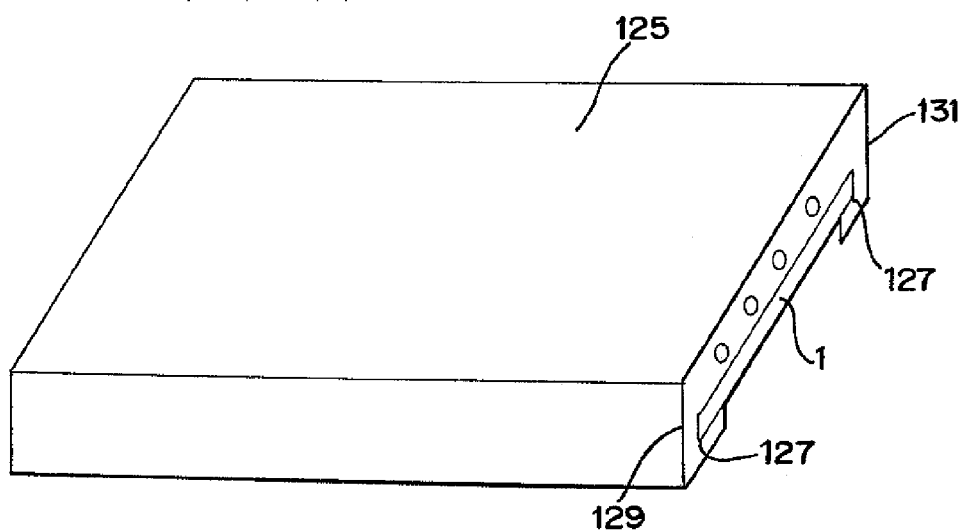
FIG. 12 illustrates an alternative method of clamping an interface device to a microarray substrate.

Although it would be possible to permanently attach the interface device to the substrate, it is presently considered preferable to provide for temporary sealing of the interface device to the microarray substrate, so that some or all processing steps can be performed with the use of the interface device, but so that the slide, once processed, can be separated from the interface device and read with any of the various existing slide reading technologies. Various methods of clamping the device together may be devised, and are considered to fall within the scope of the invention. For example, C-channel clamps such as those used in FIGS. 2 and 30 may be used. Other examples include those depicted in FIGS. 11 and 12. In FIG. 11, interface device 3 is positioned with respect to microarray slide 1 and secured with clip 121. Other types of clips or clamping devices could be used, as well. A gasket 123 having opening corresponding to channels or wells in the interface surface of interface device 3 may be positioned between interface device 3 and microarray slide 1 to form a better seal. Alternatively, as shown in FIG. 12, an alternative interface device 125 may include slots 127 in opposing side walls 129 and 131 that are sized to receive the edges of microarray slide 1 so that interface device 125 can be slid onto microarray slide 1 and thus secured thereto. As shown in FIG. 11, in order to achieve correct alignment of interface device 125 with microarray slide 1, one or more lenses 133 may be included in interface device 125 to allow for optical alignment by visualization of an alignment marking on microarray slide 1 through lens 133. In instrument-based systems in which the reaction device formed of the microarray slide and interface device are connected to an instrument, a clamp may be provided that clamps the interface device and microarray slide down to the instrument and at the same down holds the interface device in sealing relationship with the microarray slide.

Figure 13:
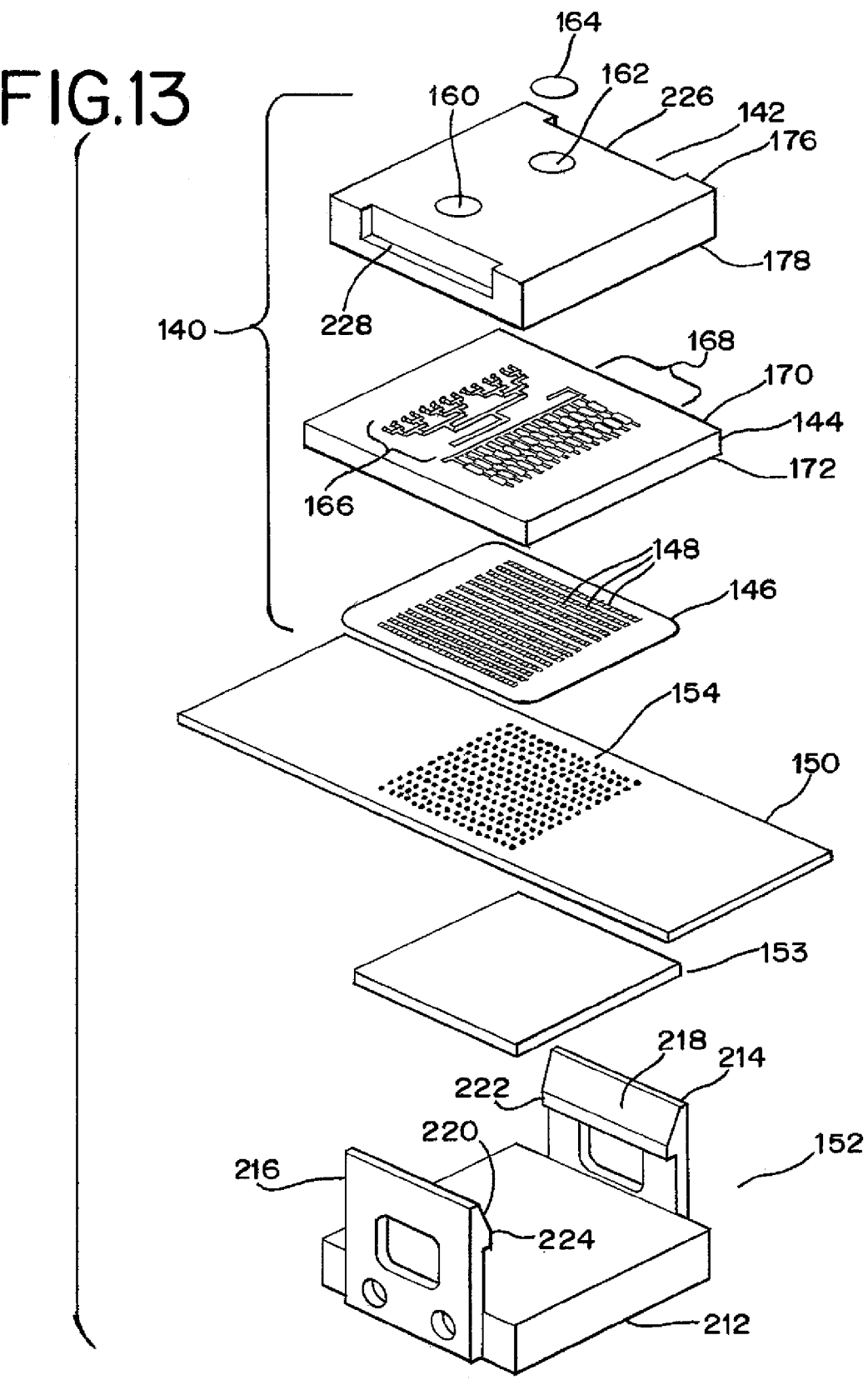
FIG. 13 is an exploded view of a further exemplary embodiment of the interface device.

FIGS. 13-22 depict another embodiment of the invention, which utilizes yet another clamp mechanism, and illustrates a number of other possible features that may be included in the invention. In the embodiment of FIG. 13, interface device 140 is formed of I/O layer 142, microfluidic circuitry layer 144, and gasket 146. In this embodiment of the invention, gasket 146 contains parallel slots 148. Parallel slots 148 define interface channels on microarray slide 150, with the height of the interface channels determined by the thickness of gasket 146 and the top and bottom surfaces of the interface channels defined by the underside of interface device 140 and microarray slide 150. The various components of interface device 140 are assembled to each other and to microarray slide 150 and secured with clamp member 152. Interface device 140 and microarray slide 150 are assembled as follows: gasket 146 is positioned with respect to microarray 154 on microarray slide 150, and removably secured thereto. Microfluidic circuitry layer 144 is positioned with respect to gasket 146, and I/O layer 142 of interface device 140 is then positioned with respect to microfluidic circuitry layer 144, and thus with respect to gasket 146 and microarray 154. The layered structure thus assembled is secured together by means of clamp member 152 or an alternative clamping structure. A resilient member 153 is located between clamp member 152 and microarray slide 150 so that microarray slide 150 is held safely and securely. The present invention is not limited to any particular clamping structure or mechanism.

Microarray slide 150 is, as described in connection with previous embodiments of the invention, a planar slide having biomolecules or other reactants immobilized thereon.

In the example shown in FIG. 13, inlet 160 and outlet 162 are formed in I/O layer 142. Inlet 160 is a large volume opening that could, for example, be threaded to receive a fitting or adapter for connection with a tube for delivering samples and reagents to interface device 140. Outlet 162 has dimensions similar to those of inlet 160; in addition, it may include hydrophobic membrane 164 to permit escape of air while preventing the escape of fluids. The inventive device may include various types of inlets and outlets, including hydrophilic capillary inlets, inlets or outlets sized to provide pipette tip access. The inlet may be formed directly in I/O layer 142 or formed separately and glued, press fit, or otherwise secured in I/O layer 142. Alternatively, one or both of inlet 160 and outlet 162 could instead be formed or secured in microfluidic circuitry layer 144.

Figure 14:
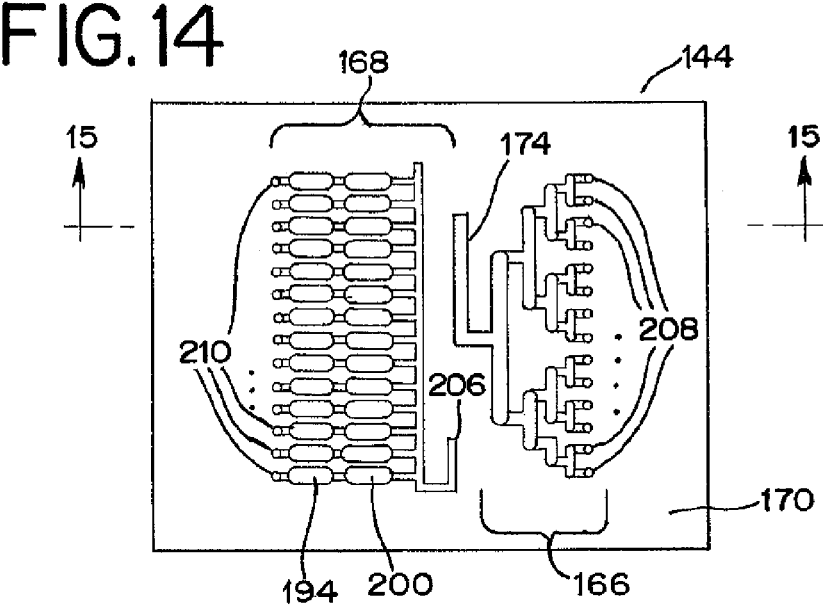
FIG. 14 is a top view of the microfluidic circuitry layer of the embodiment of the invention in FIG. 13.
Figure 15:
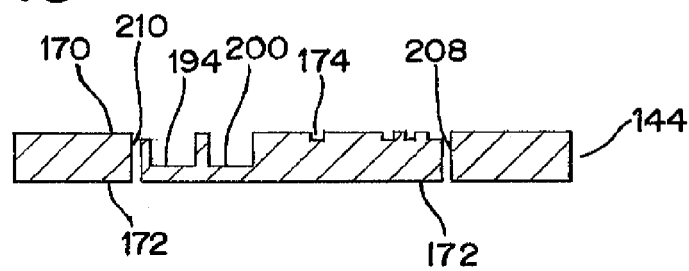
FIG. 15 is a cross sectional view of the microfluidic circuitry layer taken along section line 15-15 in FIG. 14.
Figure 17:
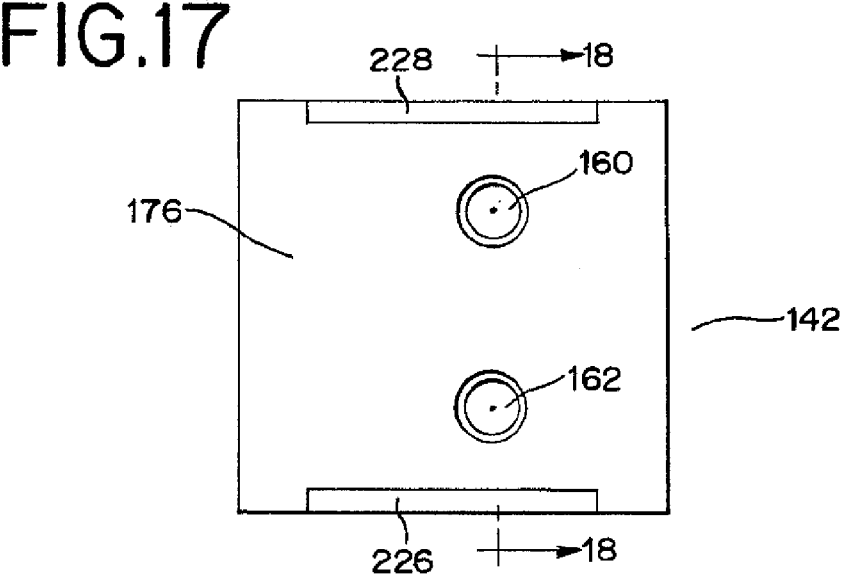
FIG. 17 is a top view of the I/O layer of the embodiment of the invention in FIG. 13.
Figure 18:
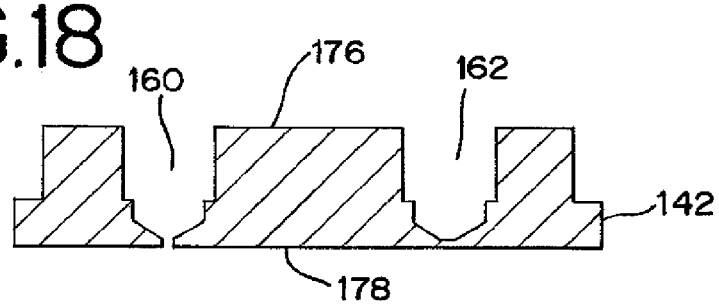
FIG. 18 is a cross sectional view of the I/O layer taken along section line 18-18 in FIG. 17.

The pre-array microfluidic circuitry 166 and post-array microfluidic circuitry 168 of the present example of the invention is formed in the upper surface 170 of microfluidic circuitry layer 144, as depicted in FIGS. 14-15. Fluid is introduced into inlet channel 174 of pre-array microfluidic circuitry 166 via inlet 160, which passes through I/O layer 142 from upper surface 176 to bottom surface 178. The structure of I/O layer 142 is shown in FIG. 17 and 18.

Figure 19:
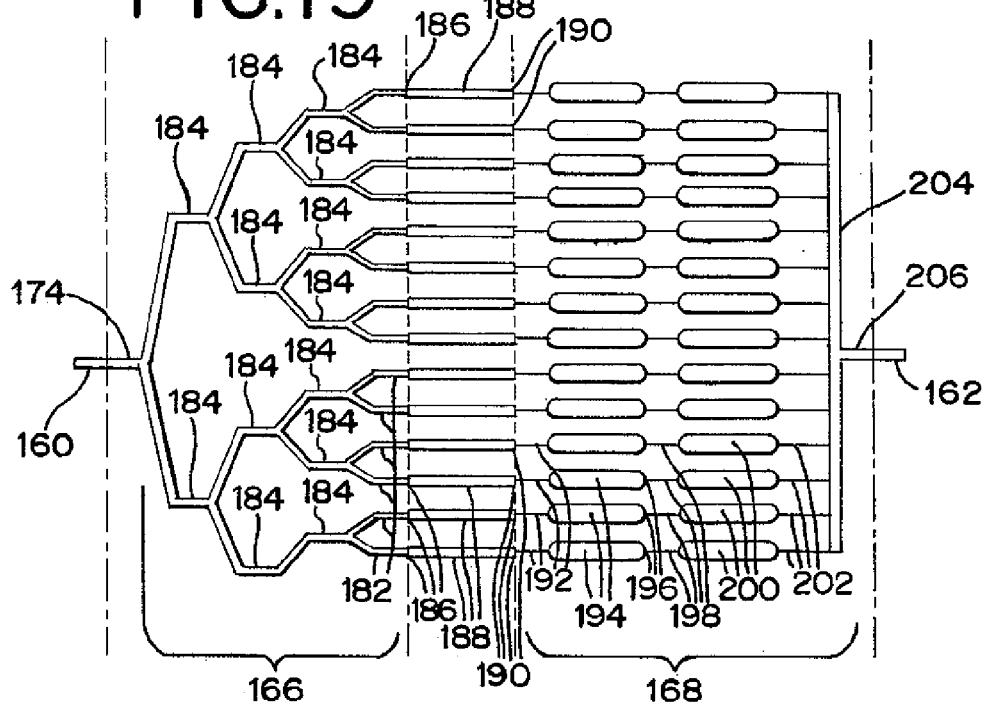
FIG. 19 is a schematic diagram of the microfluidic circuitry of the embodiment of the invention depicted in FIG. 13.
Figure 20:
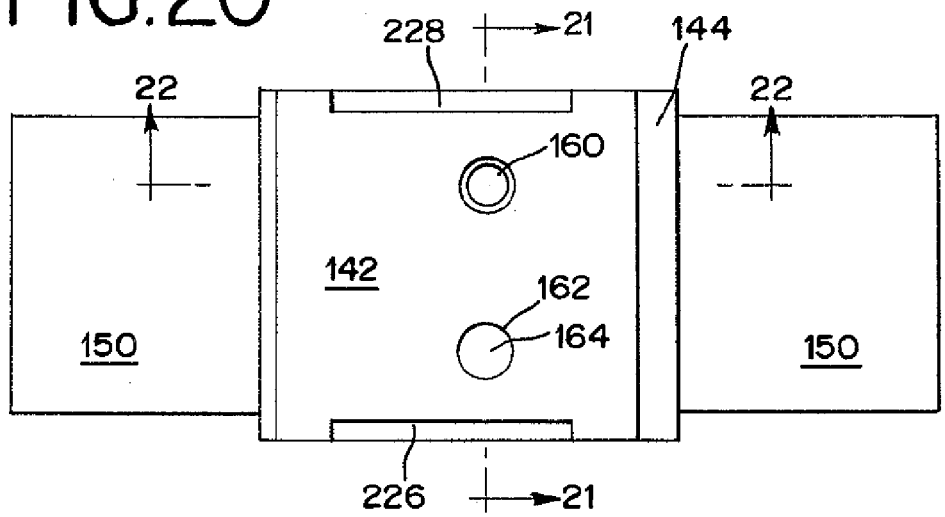
FIG. 20 is a top view of the assembled I/O layer, microfluidic circuitry layer, and microarray slide.
Figure 21:
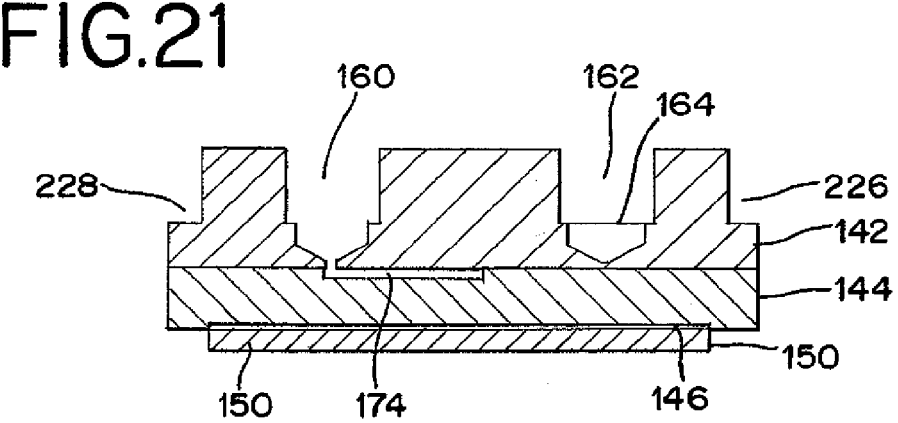
FIG. 21 is a cross sectional view taken along section line 21-21 in FIG. 20.

FIG. 19 is a schematic diagram of the microfluidic circuitry of the embodiment of the invention in FIGS. 13-18. This microfluidic circuit is designed to divide a fluid stream and deliver to multiple interface channels. The two sets of wells located downstream of the interface channels function in cooperation with passive valves at the outlets of the interface channels and the outlets of the wells to make it possible to provide controlled delivery of three fluids in sequence to the interface channels. The fluids could be, for example, a sample solution followed by two rinses or a sample solution followed by a reagent and a rinse solution, or any other combination of fluids as required by the reaction that is to be carried out. The first fluid enters at inlet 160, flows through inlet channel 174, and is divided into fourteen fluid streams 182 by microfluidic circuitry having a four-level binary bifurcation pattern. Fourteen streams, rather than sixteen, are obtained because one third level branch is omitted. At each bifurcation point 184, the channel size decreases. The step decrease in channel size produces an increased resistance to fluid flow which functions as a passive valve. Providing the step change in resistance to flow is large enough, fluid will fill all branches at each level before overcoming the resistance to flow and entering branches at the next level.

Passive valves located at inlets 186 to interface channels 188 prevent fluid from filling interface channels 188 until fluid has advanced to the inlets 186 of all interface channels. Interface channels 188 thus are filled substantially simultaneously with the first fluid. Fluid fills each interface channel 188 and stops at outlet 190 of the interface channel because of the smaller size (and thus higher resistance to fluid flow) of outlet channel 192 relative to interface channel 188.

When the second fluid is injected into inlet 160, the first fluid moves from each interface channel 188, through outlet channel 192 and into first reservoir 194, to just fill first reservoir 194 and be stopped at outlet 196 of reservoir 194. Reservoir 194 is sized to receive all of the first fluid from interface channel 188, so that interface channel 188 then fills with the second fluid. Again, all interface channels 188 will fill with the second fluid before fluid in the system moves beyond outlet 196 of any of the multiple reservoirs 194.

Similarly, when the third fluid is injected into inlet 160, to the interface channels 188, the second fluid moves into first reservoir 194, and the first fluid moves into second reservoir 200. As fluid moves into the system, air escapes via an air escape channel 202 leading from each second reservoir 200. The individual air escape channels join main air escape channel 204, which joins outlet channel 204, and subsequently outlet 162.

As illustrated in FIGS. 13-15, pre-array microfluidic circuitry 166 and post-array microfluidic circuitry 168 in upper surface 170 of microfluidic circuitry layer 144 are connected by via holes 208 and 210, respectively, to the lower surface 172 of microfluidic layer 144. As shown in the cross-sectional view in FIG. 21, via holes 208 and 210 align with and deliver fluid to the inlet ends 186 and outlet ends 190 of interface channels 188 formed by slots 148 in gasket 146. To simplify alignment of via holes 208 and 210 and slots 148, the ends of slots 148 could be made larger (giving each slot 148 a dumbbell shape) to increase the area in which via holes 208 and 210 can be positioned. The ends of slots 148 could be staggered if necessary to provide additional space for the enlarged ends.

In certain applications of the interface device, it may be desirable to rinse microarray slide 150 with a large volume of buffer or other rinse material after processing. The rinse volume may be larger than can be contained in reservoirs in interface device 140, in which case interface device 140 must include a fluid outlet to permit rinse and other fluids to be released and collected after passing through interface device 140.

In order to position gasket 146 with respect to microarray 154, spots in microarray 154, which may be relatively transparent and invisible to the naked eye, may be visualized through the use of polarization fringes or interference fringes. Gasket 146 is positioned manually, or mechanically with a micro manipulation device. Gasket 146 may be provided with a sticky or tacky material or adhesive on some or all of its lower surface, such that it may be moved for positioning with respect to microarray slide 150, but, once in a suitable position, can be removably secured to microarray slide 150 by applying pressure over the regions bearing the adhesive material. A suitable adhesive material may be, for example silicone or a pressure sensitive adhesive.

Figure 16:
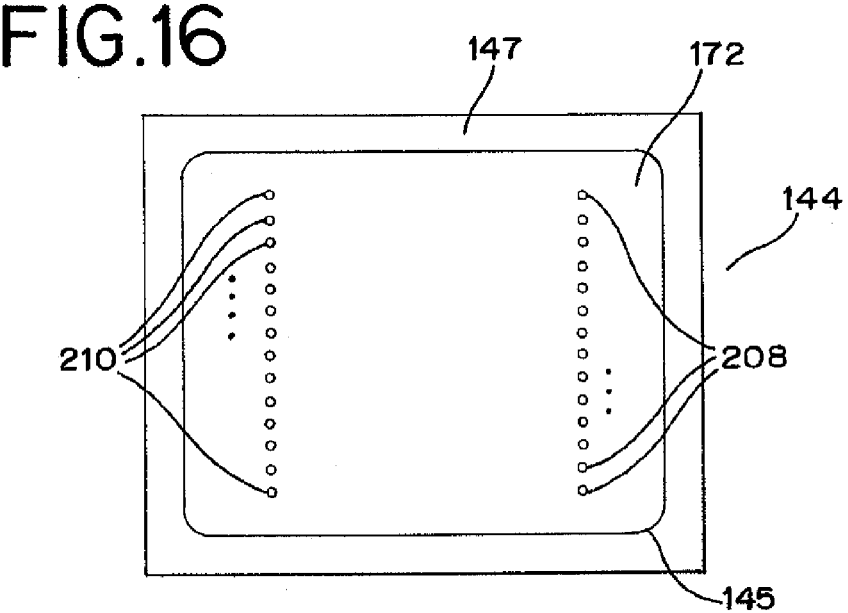
FIG. 16 is a bottom view of the microfluidic circuitry layer of the embodiment of the invention in FIG. 13.
Figure 22:
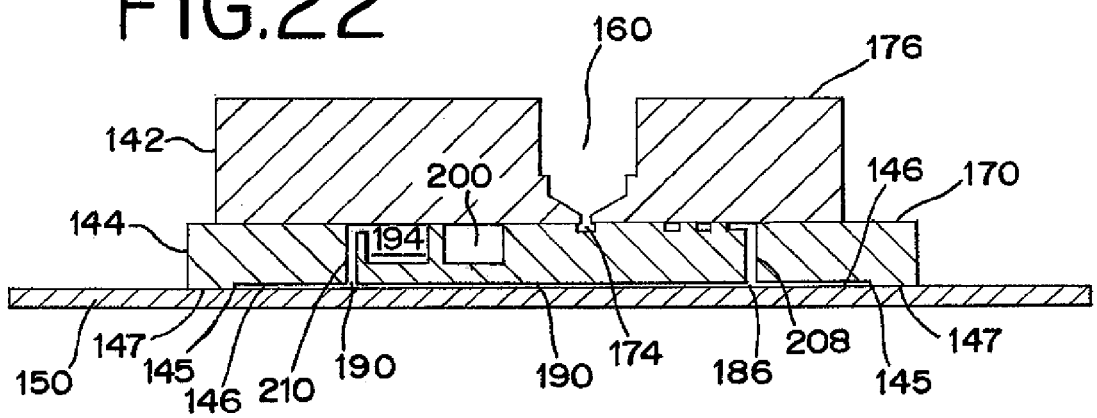
FIG. 22 is a cross sectional view taken along section line 22-22 in FIG. 20.

Alignment of microfluidic circuitry layer 144 with respect to gasket 146 may be accomplished by various methods. Microfluidic circuitry layer 144 and gasket 146 may be sized so that alignment can be achieved by aligning two or more edges of the devices. Alternatively, microfluidic circuitry layer 144 may be provided with a recess 145 into which gasket 146 fits when properly aligned, as shown in FIGS. 16 and 22. As seen in FIG. 16, recess 145 is surrounded by rim 147, which in this example forms a continuous wall around the recess, but which could have gaps, rather than being continuous. In order to permit gasket 146 to compress slightly to provide a good fit between microarray slide 150 and microfluidic circuitry layer 144, it is preferable that the depth of recess 145 be slightly less than the thickness of gasket 146. Therefore, in this embodiment of the invention it is not necessary or desired that rim 147 of microfluidic circuitry layer 144 seal against microarray slide 150, since the sealing function is provided by gasket 146.

Alignment of I/O layer 142 with respect to microfluidic circuitry layer 144 may be accomplished by several possible methods, as well. I/O layer 142 and microfluidic circuitry layer 144 may be sized so that alignment can be achieved by aligning two or more edges of the devices. Alternatively, one of I/O layer 142 and microfluidic circuitry layer 144 may be provided with one or more pegs or projections that mate with corresponding holes or recesses in the other one of I/O layer 142 and microfluidic circuitry layer 144. In yet another alternative embodiment, both layers may include aligned holes through which alignment posts can be passed. In still another alternative embodiment, lower surface 178 of I/O layer 142 may include a recess sized to receive microfluidic circuitry layer 144, comparable to recess 145 in the underside of microfluidic circuitry layer 144.

Referring back to FIG. 13, clamp member 152 includes base plate 212 and upwardly extending prongs 214 and 216 that splay resiliently outward when downward pressure is applied to angled faces 218 and 220, respectively. I/O layer 142 is pushed down far enough that projection 222 on prong 214 and projection 224 on prong 224 fit into recesses 226 and 228 on either side of I/O layer 142. Resilient member 153 between base plate 212 and microarray slide 150 provides upward bias force to microarray slide 150, which is transmitted through gasket 146 and microfluidic circuitry layer 144 to press I/O layer 142 against the underside of projections 222 and 224 on prongs 214 and 216, respectively, thus securing interface device 140 to microarray slide 150.

Interface device 140 is adapted to be removed from microarray slide 150 following processing of the slide, to allow microarray slide 150 to be read in a regular slide reader. In this case, microarray slide is preferably washed to remove reactants, processing chemicals, and so forth, prior to removal of interface device 140. The final processing step carried out in interface device 140 would thus be a high volume wash so that only buffer remains on microarray slide 150. In addition, air or gas (e.g., nitrogen) may be flowed through interface device to dry microarray slide 150 after rinsing.

Figure 23:
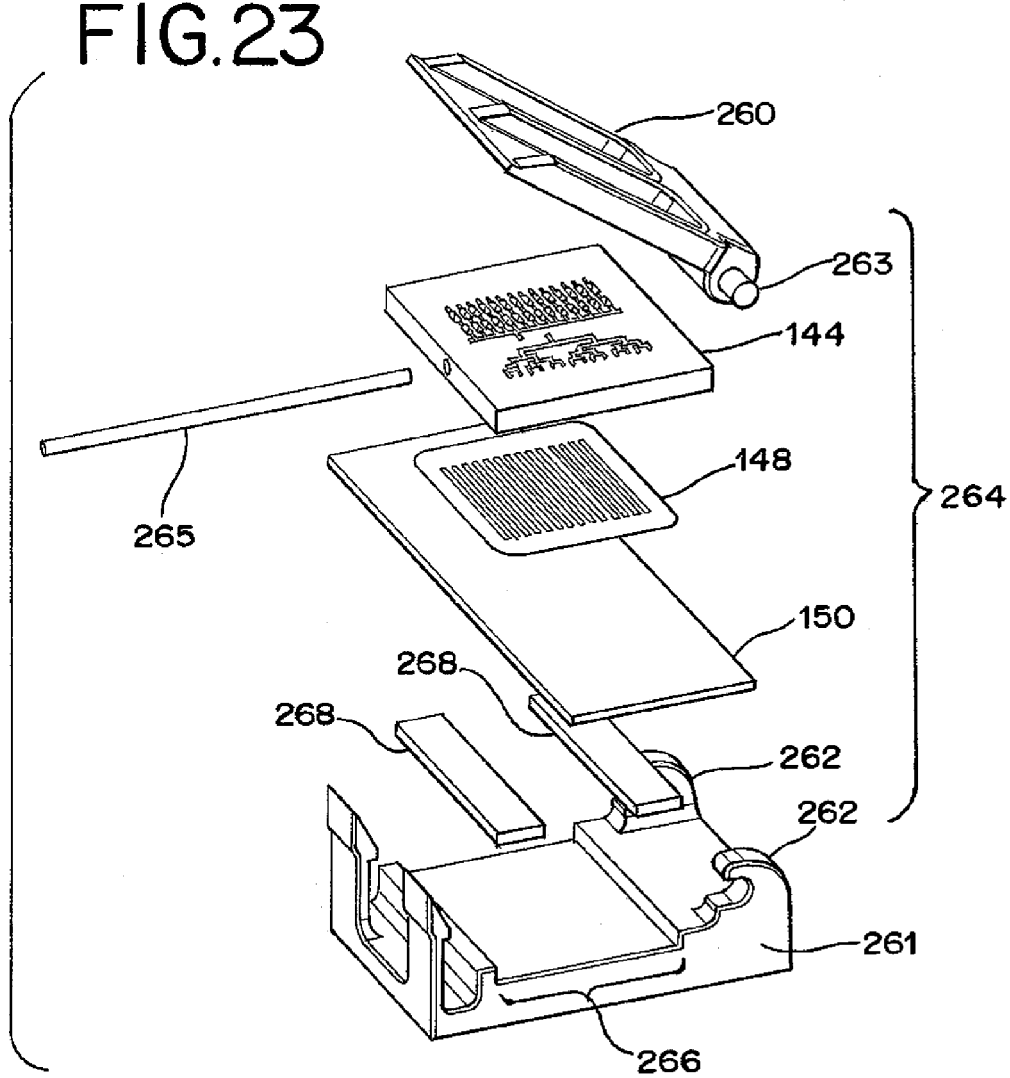
FIG. 23 is an exploded view of another embodiment of the interface device showing alternative clamping and fluid inlet designs.
Figure 24:
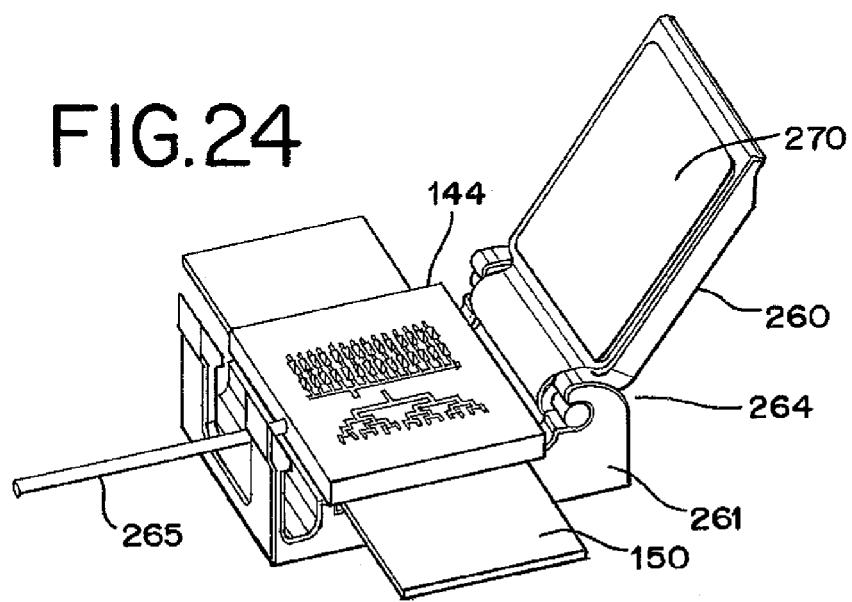
FIG. 24 is an assembled view of the device of FIG. 20.

An alternative clamp mechanism is shown in FIGS. 23 and 24. In this alternative embodiment, I/O layer is 142 is omitted. In the embodiment of FIGS. 13-22, I/O layer 142 performs two functions: the first is to serve as a lid and, in combination with the clamp member, to hold the various layers of the interface device together. The second is to provide for the introduction of fluid and release of air from the device. In the embodiment of FIGS. 23 and 24, these two functions are performed by separate elements. A hinged lid 260 is provided which clamps down on and seals the surface of microfluidic circuitry layer 144. The lid is connected to the base 261 of the clamp mechanism by a hinge 264. The fluid introduction function is performed by a hydrophilic capillary tube 265 that leads into microfluidic circuitry layer 144 and connects to inlet channel 174. The microarray slide and gasket are formed as described in connection with FIGS. 13-22. The base 261 of the clamp member includes a groove 266 for slide alignment, and, in this example, includes two strips 268 of resilient material between the base of the clamp member and the microarray slide. Likewise, the underside of the lid includes a layer 270 of a resilient material, such as silicone, which provides for a good seal and forms a top surface for the microfluidic circuitry in microfluidic circuitry layer 144. It may also be desirable, and in some cases preferable, to include a thin layer of material over the upper surface of microfluidic circuitry layer, which would form the top layer of the microfluidic channels and prevent contamination of the underside of the lid by the materials contained within the microfluidic channels. Although FIGS. 23 and 24 depict an independent device, it will be appreciated that a plurality of clamp mechanism of this type could be incorporated into an instrument of the type shown in FIG. 1, to secure multiple microarray slides, each in combination with an interface device, to the instrument.

Figure 31:
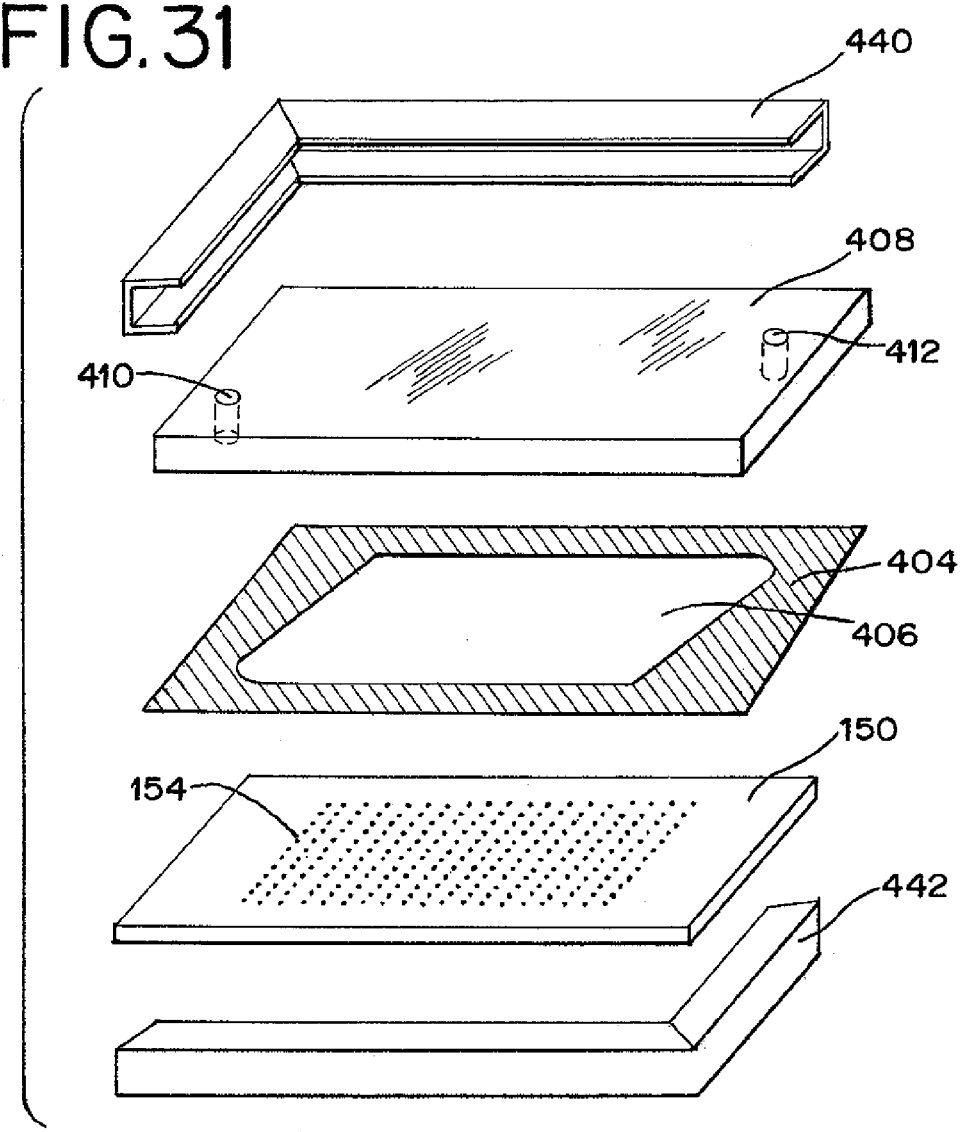
FIG. 31 is an exploded perspective view of an alternative embodiment of the invention.
Figure 32:
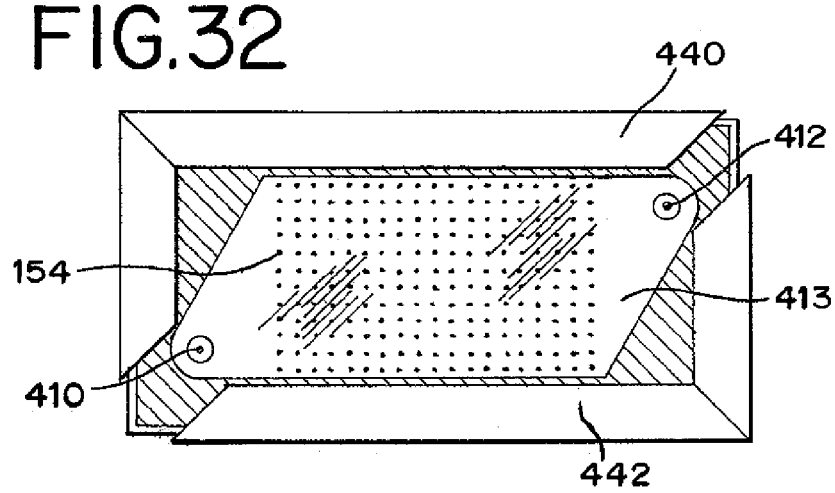
FIG. 32 is a top view of the assembled device of FIG. 31.

FIGS. 31 and 32 show another embodiment of the inventive device, similar to that shown in FIG. 30, except that opening 406 in gasket 404 is asymmetrical and clamp members 440 and 442 are not mounted to base 402. FIG. 31 depicts an exploded perspective view of the device, while FIG. 32 is a top view of the assembled device. In this embodiment, no base is provided, and clamp members simply clamp together interface device 412 and microarray slide 150, with gasket 404 positioned in between to provide sealing and form an interface channel containing microarray 154. Interface device 412 includes inlet 410 and outlet 412, which provide access to the interface channel 413. Interface device 412 is preferably formed of a transparent material to permit visualization of interface channel 413. Clamp members 440 and 442 are preferably each formed from a single piece of c-channel material which has been notched and bent to form an L-shape to provide clamping along adjacent long and short edges of interface device 412 and microarray slide 150.

In certain applications it may be desirable to mix or recirculate fluid within the interface channels during processing. For example, if the microarray is used to detect materials that occur in low concentrations in the liquid sample, the amount of time needed for molecules in the liquid sample to diffuse to spots in the microarray may be larger than is convenient, and the binding (and subsequent detection) of low concentration materials will be enhanced by providing mixing.

Figure 28:
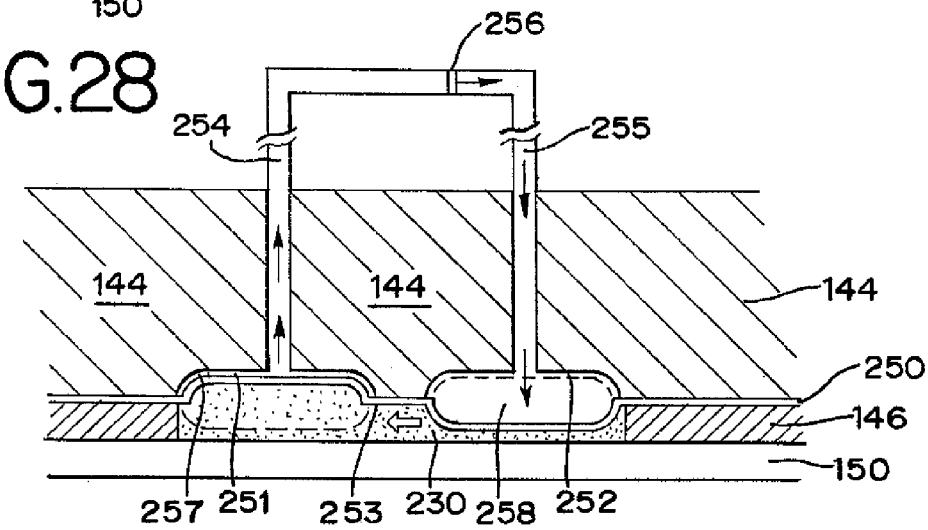
FIG. 28 depicts a system for mixing fluid on the microarray, within the array interface.

If a whole-array reaction chamber is used, of the type depicted in FIG. 25 or 27, mixing of fluid can be achieved by moving fluid back and forth across the array to bring low concentration material in the sample solution within a short diffusion distance of each spot in the array. One mechanism for achieving mixing is shown in cross section in FIG. 28. This is the same mixing mechanism used by the slide processing device illustrated in FIGS. 1-3, with slightly different design of the interface device. In both version, two air bladders are alternately inflated and deflated; in the version of the invention depicted in FIG. 28, the lower surface of the air bladders is formed by a flexible diaphragm layer, while in the embodiment of FIGS. 1-3, the lower surface (as illustrated) is formed of the same material as the main interface layer (analogous to microfluidic circuitry layer here). Referring now to FIG. 28, a flexible diaphragm 250 is positioned between gasket 146 and microfluidic circuitry layer 144. Diaphragm 250 is secured to one or both of gasket 146 and microfluidic circuitry layer 144, except at recess 251 and recess 252 formed in microfluidic circuitry layer 144 above reaction chamber 230. Recess 251 and recess 252 overlay opposite sides of one surface of reaction chamber 230. Recess 251 and recess 252 are separated by divider 253, to which diaphragm 250 is connected to form separate air reservoirs (i.e., air bladders) 257 and 258. Air reservoirs 257 and 258 communicate with air channels 254 and 255, respectively, but not with each other. A pressure source 256 generates a positive pressure in one air reservoir, while generating a negative pressure in the other. In the example of FIG. 28, positive pressure in air reservoir 258 drives diaphragm 250 outward, while negative pressure in air reservoir 257 draws diaphragm 250 inward, thus generating movement of fluid in reaction chamber 230 in the direction indicated by the white arrow. Pressure source 256 could be a piston, as indicated in FIG. 28, or a peristaltic pump, or comparable device. Pressure changes in air channels 255 and 256 are preferably of equal amplitude but opposite sign, but may be generated by various means, by a single pressure source or by independent pressure sources. By alternately expanding and contracting air channels 255 and 256, fluid is moved back and forth in reaction chamber 230. As illustrated and described in connection with FIG. 1, a manifold may be used to distribute a pressure signal from a single source among multiple reaction devices.

Another method for providing mixing or agitation is to use piezoelectric actuators. Piezoelectric actuators can be mounted in or on either interface device (e.g., 408 in FIG. 30), on microarray slide 150, or in base 402. Alternating electrical potential applied across a piezoelectric actuator causes it to vibrate at the frequency of the alternating potential. The alternating potential may be a sinusoid, square wave, triangle wave, or other waveform. Piezoelectric actuators may be attached to interface device 408 or base 402 by various method known to those of ordinary skill in the relevant art, for example UV curable epoxy or mechanical clamping. Electronic circuitry used to control piezoelectric actuators in base 402 or interface device 408 would preferably be connected piezoelectric actuators by wires by located in an external control module. One exemplary configuration would be for base 402 to include two piezoelectric actuators operating 180 degrees out of phase with each other and positioned at a distance from each other in order to generate vibration and mixing within interface channel. Another alternative would be to use three piezoelectric actuators operating 120 degrees out of phase with each other. However, the invention is not limited to any particular number of piezoelectric actuators or any particular phase relationship between signals used to drive the actuators.

Figure 29A:
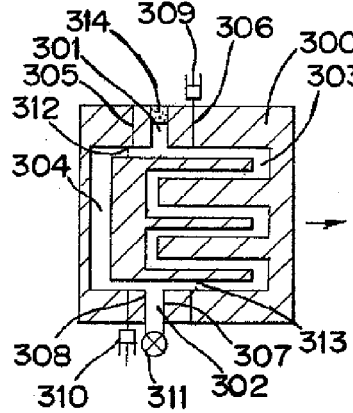
FIG. 29A shows a first step of a microfluidic fluid circulation process.
Figure 29B:
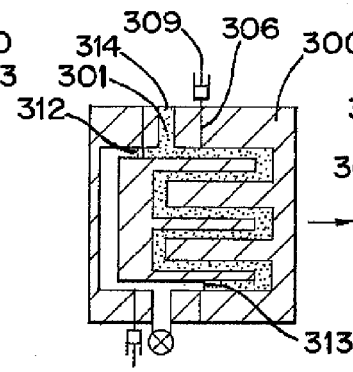
FIG. 29B shows a second step of a microfluidic fluid circulation process.
Figure 29C:
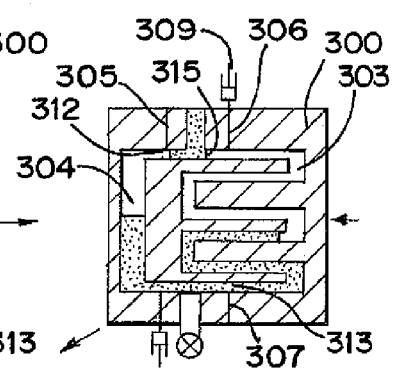
FIG. 29C shows a third step of a microfluidic fluid circulation process.
Figure 29D:
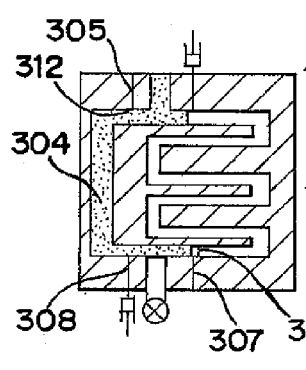
FIG. 29D shows a fourth step of a microfluidic fluid circulation process.

Another method for mixing fluid is to recirculate fluid over the microarray by connecting multiple interface channels in series, forming a single, serpentine channel that communicates with all rows of the array. Fluid can be recirculated through the serpentine channel. One embodiment of a microfluidic recirculator, and its method of use, is illustrated in FIGS. 29A-29B. FIG. 29A depicts a fluid circuit 300 with an inlet 301, an outlet 302, a forward fluid path 303 and a return fluid path 304. The fluid circuit contains air ducts 305-308. Ducts 305 and 307 are simple ducts that are always open, whereas 306 and 307 have air pumps 309 and 330 connected to them that are designed to inject air into the fluid circuit. Downstream valve 311 is a valve connected to outlet 302 that is used to control the displacement of fluid and air out of the fluid channel. Downstream valve 311 is connected somewhere downstream of 302. Passive valves 312 and 313 are two hydrophobic restrictions that act as stopping means. Other types of passive valves, such as hydrophilic restrictions, may also be used. 314 is the sample or fluid that is being pushed through the fluid circuit using some form of pumping means. The forward path 303 is a serpentine channel, but can be any channel configuration. The return path 304 is shown to be more direct, but can also be serpentine, or any other type of path. Forward path 303 and return path 304 define a loop channel which is necessary in order for fluid to be circulated. The volumes of the forward channel 303 and return channel 304 between the inlet 301 and outlet 302 should be somewhat equal. For most of the recirculating process, the downstream valve 311 is closed, indicated by a circle with a cross in it. For the last step shown in FIG. 29G, where fluid is pumped out of the recirculated path, downstream valve 311 is shown in an open configuration as indicated by the circle with an open channel in it.

In FIG. 29A, the fluid 314 is entering the circuit for the first time. In FIG. 29B, the fluid 314 is pumped further into the circuit. The fluid does not flow past the passive valve means 312 because it generates a barrier to flow. The fluid is pumped to the second passive valve 313. The fluid may not reach 313, but it should definitely not be pushed through it at this stage. The volume of fluid delivered may be controlled by knowing the volume of the fluid circuit and displacing that exact volume, or by a pressure feedback mechanism that indicates when both passive valves 312 and 313 have been encountered, or by a sensor that is able to detect when the fluid reaches 313, or by some other means.

In FIG. 29B, once the fluid reaches or nears 313 the fluid pumping stops. Air is displaced into the fluid circuit via the pump 309 and air valve 306. In the FIGS. 29C and 29D, the air pushes the fluid through passive valve 313, which is designed to be a weaker barrier than passive valve 312. Once air pump 309 has pushed the fluid past passive valve 313, the pumping stops. The air that is displaced on the return path 304 escapes the system via the air duct 305. Both air ducts 305 and 307 are immediately adjacent to the passive valves so that air can re-set the valve, but not push the fluid too far away from the valve because it is desired that the valve be wetted through so as to eliminate the barrier, such as at 312 in FIG. 29D.

Figure 29E:
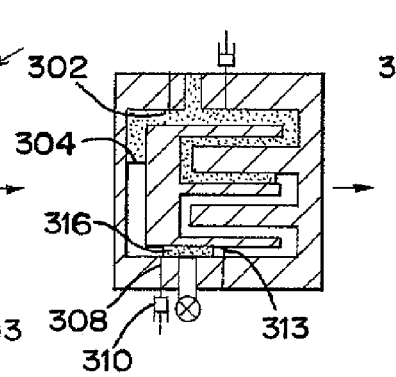
FIG. 29E shows a fifth step of a microfluidic fluid circulation process.
Figure 29F:
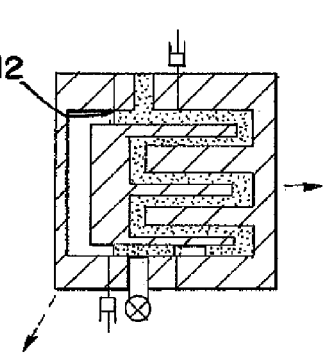
FIG. 29F shows a sixth step of a microfluidic fluid circulation process.
Figure 29G:
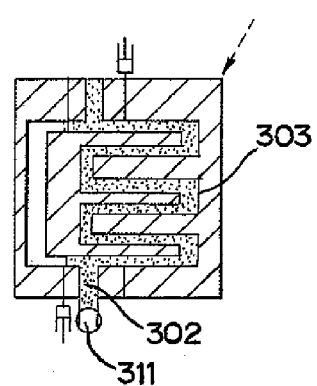
FIG. 29G shows a seventh step of a microfluidic fluid circulation process.

In FIG. 29E, once passive valve 313 is re-set, the air pump 130 injects air into the circuit via air duct 308 to push the fluid through the return path 304. The pump 130 pushes the fluid until it is pushed past passive valve 312, thus re-setting that valve, as shown in FIG. 29F. At this point the fluid can be recirculated again, or the outlet valve 311 can be opened and the fluid pumping can resume to push all of the fluid in the forward path 303 out of the circuit, as in FIG. 29G. It is also possible that the fluid may be pumped out through both branches 303 and 304 of the circuit instead of just the forward path 303. The plug of fluid, 315 in FIG. 29C and 316 in FIG. 29E, serves as a physical barrier to air flow down the wrong channel.

It is frequently desirable to minimize the volume of an interface channel, in order to minimize the amount of sample required for processing the microarray. However, interface channels or wells that cover a relatively large portion of a microarray slide must be extremely shallow in order to give the desired low sample volumes. Limitations on the smoothness of components formed by molding and machining make it difficult to obtain a chamber having a uniformly low depth. In one aspect of the present invention, a filler material is flowed into an interface channel having a larger-than-desired volume to either temporarily or permanently partially fill and thus reduce the volume of the channel. The filler may form a smoother and more uniform interior surface than could be obtained otherwise The filler material may be a liquid filler 454 that is immiscible with the sample 450 that is to be passed through the channel, as illustrated in FIG. 33, or it may be a material that flows into the interface channel in liquid form but which solidifies to become a solidified filler 452 that is a part of the inner surface of the interface channel, as illustrated in FIG. 34. An example of an immiscible liquid is a mineral oil or vegetable oil used in combination with an aqueous sample. An example of a filler material that would initially be in liquid form but would solidify to become a part of the inner surface of the interface channel would be a paraffin material that could be warmed to liquefy it prior to being flowed into the channel, and then cooled to solidify it. The filler material would necessarily have a melting point that was higher than the highest temperature to which it would be exposed during microarray processing, if it was to remain solid. However, it may not be necessary that the filler material remain solid so long as it is immiscible with the reactant and reagent solutions that come in contact with it. It is necessary, however, that the filler material does not adhere to the microarray slide 150 and exclude sample or reagent solutions from the vicinity of the dots on the microarray. Affinity of the filler material for the surface of the microarray slide must be considered. Likewise, the density of the filler relative to the reagent/reactant solutions used and the orientation of the microarray slide 150 with respect to the interface chamber would also need to be considered in determining whether a particular filler material could be used without interfering with the surface of the microarray slide 150.

The inventive interface device may include various types of sensors, including but not limited to fluid sensors, temperature sensors, pressure sensors, electrodes, and optical sensors for real-time detection of reactions occurring in the interface device, and for feedback control of various reaction conditions. The interface device may include heating elements or other mechanism for regulating reaction conditions. For example, heating elements may be used to perform thermo-cycling during PCR. As noted previously, the base may include heating elements. It is preferred that permanent components be included in one portion of the inventive device, while other portions of the device (e.g., the interface device) be made disposable. Control and data signals from heating elements and various sensors would preferably sent to and from an external control module via wiring.

One of the advantages of the inventive system is that it can be configured for use in processing a single slide, or it can be multiplexed to handle the processing of multiple slides. The functionality of an instrument for use in a multiplexed system, of which the embodiment of FIG. 1 is an example, will now be described in greater detail. FIG. 35 shows the preferred schematic of the invention. A user interface 618 allows the user to specify the reaction conditions provided by the invention, including heating parameters such desired temperature as well as duration of heating or cooling, and mixing parameters such as pumping pressure, mixing frequency, duty cycle, and duration of mixing (for pneumatic mixing as used in the embodiments of FIGS. 1-3 and 30). Data input at user interface 618 is transmitted to temperature controller 650 and pump controller 652, which may include components such as a microprocessor and a memory device, and which regulate parameters as set on the user interface 6. A control signal is sent from temperature controller 560 to heat block 606. A temperature feedback signal is sent back to temperature controller 650 to allow the desired temperature to be properly maintained and regulated. A pump 654 (or other pressure source), as directed by the user interface 618 and regulated by the pump controller 654, develops positive and negative pressure differentials that enter the pressure manifold 622 and are distributed to each reaction device 604 via tubes 606 and 661. Pressure differentials can be transferred through two mediums: gas (preferably air), as described herein, or liquid (preferably water). As illustrated in FIG. 1, temperature controller 650 and pump controller 652 may be packaged separately. However, as noted previously, it would also be possible for both controllers, as well pump 654, manifold 644, and heat block 606 to be packaged in the same instrument case.

If other active elements such as electrodes, active valves, piezoelectric elements, etc. are included in the interface device or in the instrument, the instrument may include one or more additional components that may receive inputs from user interface 618, and send control signals to the active elements via an electrical connection to activate them in the desired fashion. In the case the active elements are sensors such as sensing electrodes or optical or temperature sensors, etc., the additional components may receive electrical signals from the active elements via an electrical connection, and may display information concerning the signals received from the active elements on the user interface receive electrical signals from said at least one active element It would also be possible to program a computer to function as a user interface and to generate control signals to operate the heat block, pump, or other active elements used in the device.

Figure 36:
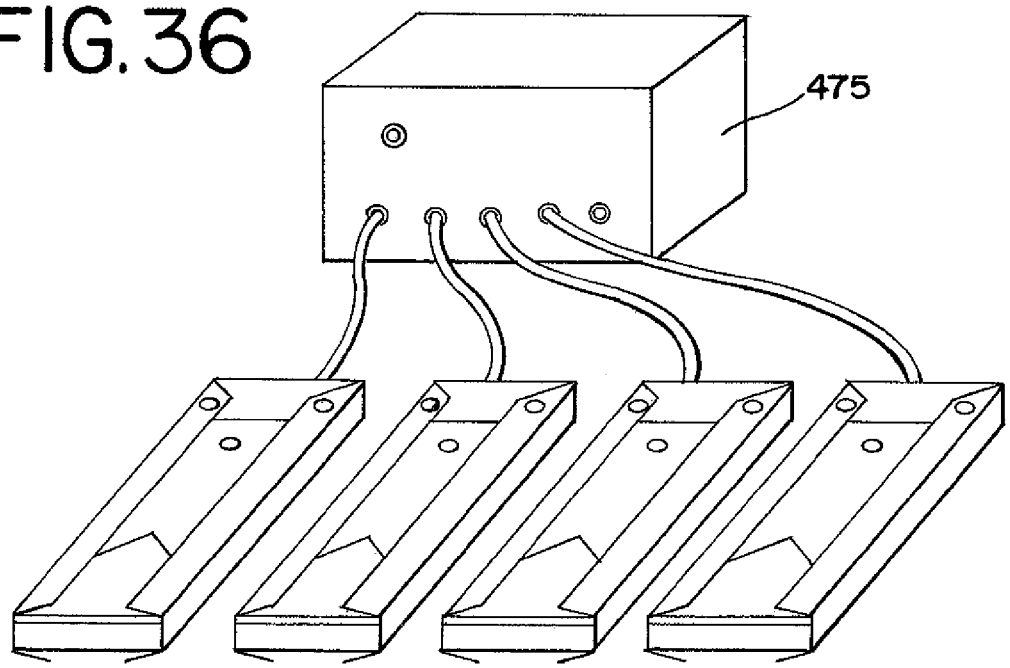
FIG. 36 is a perspective view of an external control module connected to multiple bases.
Figure 37:
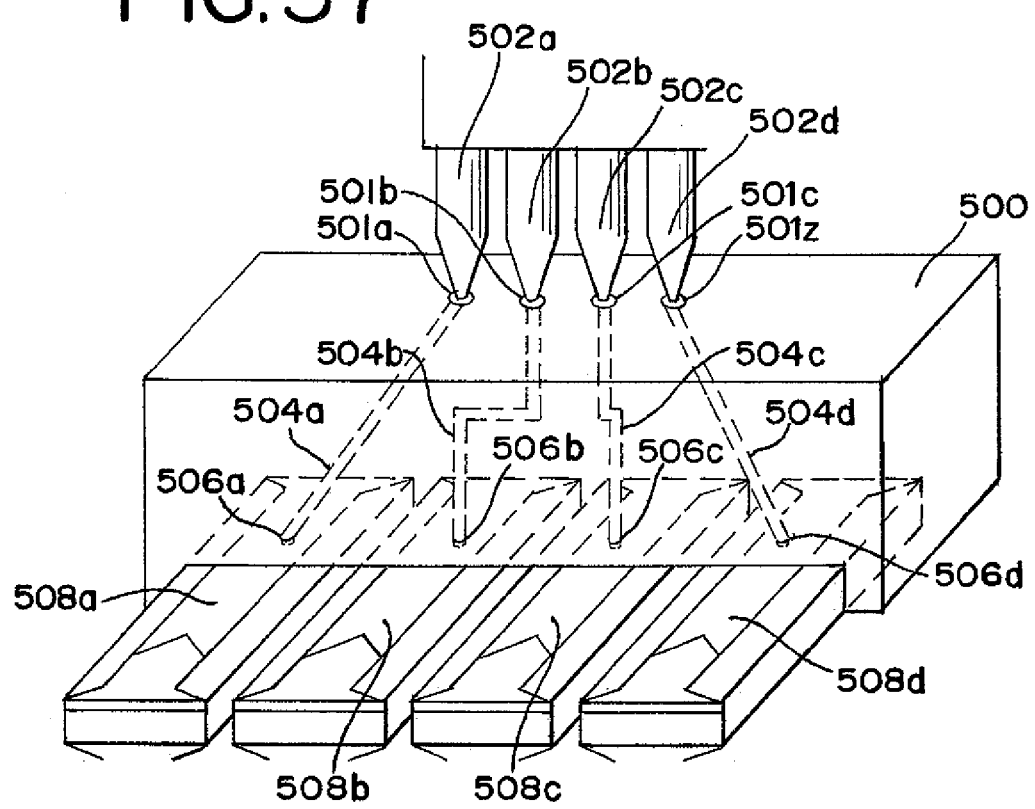
FIG. 37 is a perspective view of an adapter for delivering samples from a multipipettor to multiple interface devices.
Figure 38:
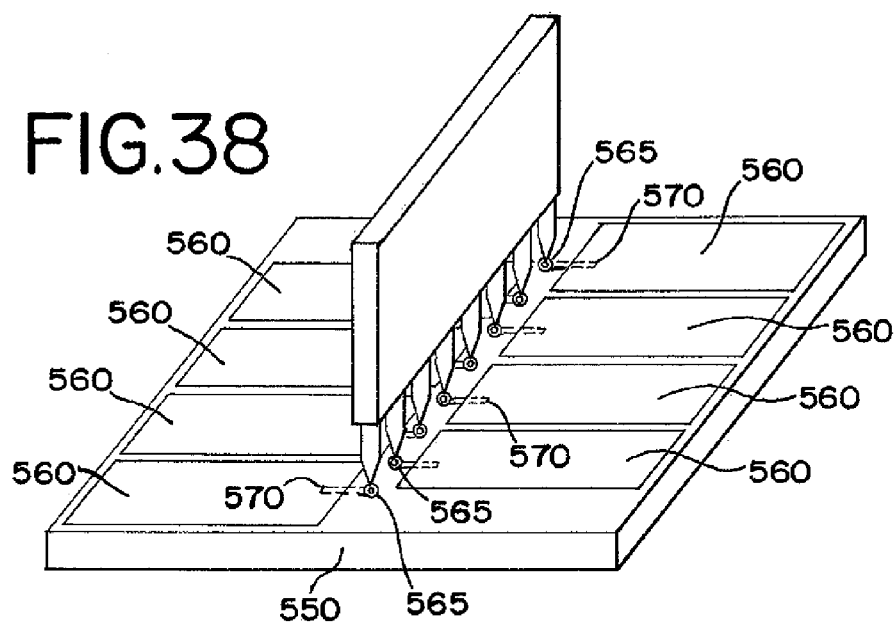
FIG. 38 is a perspective view of an instrument including an adapter for delivery of samples from a multipipettor to multiple interface devices.
Figure 39:
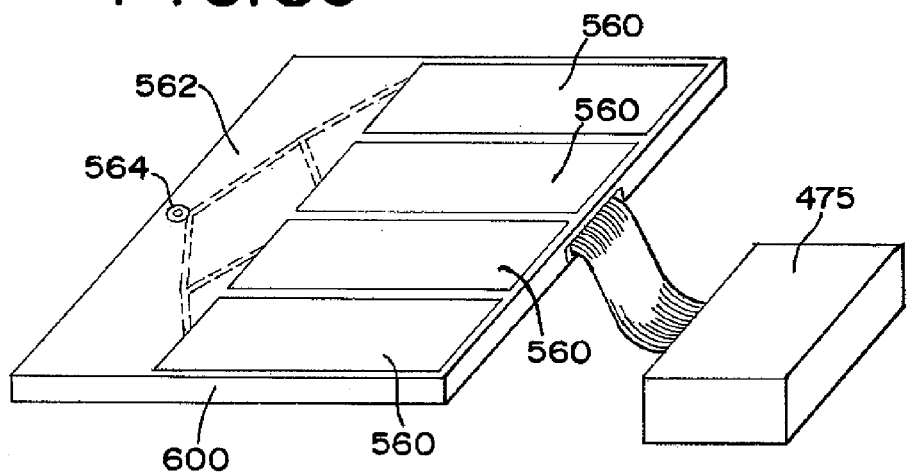
FIG. 39. is a perspective view of an instrument including a manifold for delivering a single sample to multiple interface devices.

FIGS. 36-39 depict several alternative approaches to connecting reaction device and instruments or bases. In one alternative embodiment of the invention, a single external control module controls and receives data from a plurality of bases to control heating, mixing, and other functions, which are provided in the bases, each of which is connected to a single slide and interface device, as depicted in FIG. 36. In the embodiment of FIG. 36, sample and reagent fluids are delivered manually into an opening in the upper surface of each reaction device, in the same manner as with other embodiments previously described. In other embodiments of the invention, a multi-slide instrument that accommodates multiple slides and interface devices is used, as depicted in FIG. 39. A single external control module may control one or more bases, each of which may support one or multiple slides and interface devices. Alternatively, both the base, which supports one or more slides and interface devices, and the electronics for controlling heating, mixing, and other base functions, may be incorporated into the instrument itself. In the embodiments of FIGS. 37 and 38, multiple fluid aliquots are loaded into the instrument, and from there distributed to individual reaction devices. In the embodiment of FIG. 39, a single fluid aliquot is loaded into the instrument, divided into multiple aliquots via a manifold, and delivered to multiple reaction devices seated in the instrument.

For delivering samples and reagents to a small number of slides, it is convenient for a lab technician to simply pipette sample and reagents into the inlets of an individual interface devices sealed to individual slides. However, if larger numbers of slides are processed, it is preferable that samples and reagents be delivered to slides in a more automated manner.

Multipipettor devices have been developed and are commonly used in laboratories that process large numbers of DNA samples. Such multipepettors are capable of pipetting multiple samples simultaneously into microtiter plates. Multipipettors have multiple pipette tips spaced evenly at a standard distance of (typically) 9 mm. Such multipipettor devices could be used to deliver samples to multiple slides, via interface devices according to the present invention, with an adaptor having inlets spaced to receive the pipette tips of the multi pipettor, and outlets capable of mating with inlets of the interface device. As shown in FIG. 37, adaptor 500 has a plurality of inlets 501a-501d on its upper surface, at the same spacing as multpipettor pipette tips 502a-502d. Adaptor channels 504a-504d pass through the interior of adaptor 500 to nipples 506a-506d on the underside of adaptor 500, which mate with the inlets of interface devices 508a-508d. Adaptor channels 504a-504d as shown in FIG. 37 are all of the same length, because in many cases it will be desirable to have the same volume of dead space. However, adaptor channels can be manufactured with varying lengths, if that is more convenient or more desirable in a particular application.

FIG. 38 depicts instrument 550 capable of receiving multiple slides, each with its own interface device 560. In this example, slides are positioned on either side of adaptor inlets 565, to minimize the distances between adaptor inlets 565 and inlets 570 of the interface devices.

Figure 40:
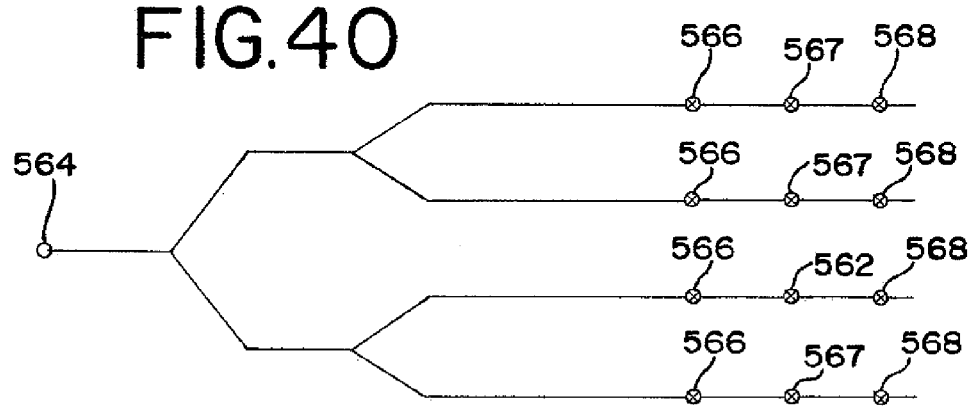
FIG. 40 is a schematic diagram of the microfluidic circuitry of FIG. 39.

FIG. 39 depicts a manifold design for distributing fluid from a single inlet 564 to multiple slides. In this example, the multiple slides and their associated interface devices 560 are secured in a single base 600, which also includes fluid manifold 562. FIG. 39 also shows an external control module 475 connected to base 600, to control heating and mixing functions included in base 600. It would also be possible to form the manifold in a structure separate from the base, comparable to adaptor 500 depicted in FIG. 37. Manifold 562 may include passive valving to achieve uniform distribution of sample among interface devices and deliver sample to each slide substantially simultaneously. A schematic diagram depicting the microfluidic circuit formed by manifold 562 and the connected interface devices 560 is shown in FIG. 40. Each interface device includes a single interface channel, with several downstream passive valves (indicated by reference numbers 566, 567 and 568. If each interface device is processed individually, the passive valving may not be functionally meaningful, but if multiple interface devices are processed in parallel, the passive valving in the individual interface devices can regulate distribution of fluid among all of the interface devices.

In another embodiment of the invention, multiple slides are processed simultaneously by stacking microarray slides and interface devices incorporating microfluidic circuitry to minimize the amount of space occupied by the slides. If desired, the underside of microarray slides can function as the top surface of microfluidic circuitry used in processing the next slide in the stack. Inlets and outlets to the microfluidic circuitry would then be made via one or more edges of each interface device, rather than via the top surface of the device.

The inventive microarray interface device facilitates delivery of samples and reagents to microarray slides to achieve on-slide processing of microarrays. As noted previously, microarray slides may include spots of molecules of interest, which may be DNA, RNA, oligonucleotides, or proteins. Although various methods are known for processing these different molecules, and in particular, methods for processing proteins will differ from methods for processing nucleic acids, nevertheless certain basic processing steps will be carried out for all microarray slides and should preferably be accommodated by the microarray interface device.

The general method of using the inventive interface device is as follows:

Microarray slides may be obtained commercially, manufactured in the lab where they are processed, or obtained by other means. Various types of slides may be used in the practice of the invention, including glass slides, including those with various types of treated surfaces, as well as plastic slides. Prior to being sealed to interface device, slides with double-stranded DNA are typically subjected to a heating step to separate double strands, followed by washing to remove unbound strands. In addition, in order to obtain good sealing between the gasket and the slide, it is preferred that the portions of the slide that will contact the gasket be smooth and clean.

The interface device is sealed to the slide by positioning slide, gasket (or other sealing means), and interface device properly with respect to each other, and clamping them together to obtain a good seal. After the interface device is sealed to the slide, the following basic steps are carried out to process the microarray slide:

1) Pre-binding—a solution that includes substances that block non-specific binding sites is introduced to the interface channel(s) via the interface device. The blocking solution may include surfactant to aid in cleaning the slide. The blocking solution may be incubated on the slide to allow complete reaction to occur. If the process to be carried out on the microarray is hybridization of nucleic acids, the blocking solution will be a pre-hybridization buffer, as known in the art, and the microarray slide will be incubated with the pre-hybridization buffer for typically 45 minutes to 2 hours at 42 degrees C.

2) Washing—a wash solution is passed through the interface channel(s) to remove extraneous materials from the microarray that could cause non-specific binding 3) Binding—a binding solution containing a molecule (or molecules) that binds selectively to molecules of interest on the microarray and either directly or indirectly generates a detectable signal is injected into the interface channel(s). The slide is then incubated with the binding solution. If hybridization of nucleic acids is being performed, the binding solution will be a hybridization solution, and the incubation will typically be performed overnight at 42 degrees C. Mixing or agitation of the solution may decrease the time required to obtain complete maximum binding. Various types of binding reactions may be carried out and subsequently detected on microarray slides, including, but not limited to, protein-protein, "drug"—protein, peptide-protein, and RNA-DNA binding reactions.

4) Washing—a second washing step is performed to remove unbound molecules from the binding solution, as well as extraneous materials which may cause noise or interference in detection of binding (e.g., SDS, typically used in pre-hybridization buffer, produces fluorescence that competes with the fluorescence produced by bound molecules of interest)

5) Detection—binding molecules from the binding solution to molecules on the microarray slide is typically determined by detecting fluorescence, radioactivity, color change, and so forth, occurring at sites where binding occurred. It is frequently the case that the binding molecule in the binding solution is labeled, for example with a fluorescent dye, so that sites where binding has occurred fluoresce, and the amount of fluorescence is a function of the number of bound molecules at a given location. Detection may be performed while the interface device is attached to the slide, providing the interface device includes a viewing window to permit visual access to the slide, or the slide may be removed from the interface device for detection to be carried out on the slide alone.

The present invention can be used to carry out binding reactions of various types of immobilized chemical compounds on a slide with binding compounds in a solution, typically with little or no modification to the basic design of the device. The main design constraints imposed by particular slide processing protocols are the need for the device to maintain a good seal during any heating steps, to provide any necessary mixing or agititation during incubation steps, and to provide sufficient waste storage volume or allow for diversion of waste to an external storage device. The steps outlined above need not all be carried out with the use of the inventive interface device. For example, blocking steps may be performed before the slide is sealed to the interface device. Similarly, the detection step may be performed after the slide is removed from the interface device. Moreover, the interface device may be used for processing slides by methods other than that described above, and the invention is considered to include the use of the interface device for processing steps other than those specifically disclosed above.

Various pre-processing modules may be connected to the inventive interface device, to perform various steps in the biochemical processing of binding compounds before they are applied to the microarray. Exemplary pre-processing modules include a separation module, a labeling module, and a purification module. The modules would preferably be connected to the interface device in series, so that a crude tissue sample would first be introduced to the separation module for purification of a binding compound (such as DNA, RNA or protein) from the crude tissue sample. Next, the purified sample would go into the labeling module for labeling and/or amplification. Finally, the labeled binding compound would go into the purification module for final cleanup prior to addition to the array. Alternatively, individual pre-processing steps could be completed manually such that the user could plug into any module in this series or add appropriately prepared sample directly into the interface device for introduction to the microarray. Waste reagents and wash solutions exiting each preprocessing module would preferably be routed from the pre-processing module directly to a waste storage container, rather than into another pre-processing module or into the microarray interface device.

A separation module would separate the compound to be provided in the binding solution from crude tissue samples or cells prior to labeling and hybridization. A crude liquid extract from cells, or tissue consisting of lipids, polysaccharides, proteins, nucleic acids, salts, and so forth would be applied directly onto this module and based on differential affinity matrices, size exclusion or dialysis principles, electrophoretic behavior, the binding molecule (RNA, DNA, or protein) would be separated from unwanted contaminants The labeling/amplification module would incorporate a fluorescent or other label onto the binding molecules that are to be hybridized to the array using the interface device. The labeling reagents can be either pre-loaded in the module (preferably in dried form) or coinjected with the sample. The labeling reactions typically include the linkage of readily detectable tags to the sample such as fluorescent or radioactive nucleotides, enzymatic molecules, and antigenic peptides or other molecules such as biotin that have affinity to readily detectable tags. Amplification steps include, but are not limited to, methods which amplify nucleic acids, such as polymerase chain reaction, rolling circle amplification, ligase chain reaction, and Eberwine amplification, or other amplification methods using various forms of DNA or RNA polymerases. These various techniques for labeling and amplification methods will hereafter and forever be referred to simply as labeling and amplification steps.

The sample purification module, which would purify sample(s) immediately prior to application to the array, would accept liquid samples containing the binding molecule, which can be DNA, RNA, or proteins and various contaminants remaining from previous biochemical steps. Contaminants could include, but are not limited to, unincorporated fluorescently labeled nucleotides, salts, polysaccharides, lipids, and proteins. The purification may be based on differential affinity matrices (immobilization of target and washing away of contaminants), size exclusion, dialysis principles, or electrophoretic behavior.

Although the embodiments of the invention depicted herein are shown in use with planar microarray slides, it is envisioned that the inventive array interface device could be adapted for use with non-planar substrates. In particular, the interface channels or wells of the interface device could have sizes and spacings which allow them to interface with substantially planar substrates such as microtiter plates having wells. In addition, an interface device according to the present invention could be constructed which would conform to and seal with substantially non-planar substrates, such as bundles of optical fibers.

The present invention is described and disclosed in connection with a number of examples. However, the scope of the invention is not limited to the specific examples provided herein, but is intended to included various modifications as may be devised by those of ordinary skill in the art, and is defined by the claims appended hereto.

The invention claimed is:

1. An interface device for interfacing to a surface of a substrate bearing a biological sample immobilized on a first surface thereof, comprising:
  a. a main interface layer having a substantially planar interface surface adapted to conform to and interface with the first surface of the substrate to which the biological sample is immobilized;
  b. a substantially planar gasket positioned at said interface surface and having at least one opening formed therethrough, wherein inside walls in the at least one opening of said gasket define the inside walls of an interface channel;
  c. an inlet channel formed in said main interface layer and opening into said at least one opening;
  d. an outlet channel formed in said main interface layer and opening into said at least one opening; and
  e. at least one air bladder formed in said main interface layer adjacent said interface surface, wherein said at least one air bladder has a flexible lower surface defined by a substantially planar flexible gas-impermeable diaphragm layer having a portion disposed between the main interface layer and the gasket and a portion defining the flexible lower surface of the air bladder, wherein the flexible lower surface is capable of being deflected outward as said air bladder is inflated or inward as said air bladder is deflated, and wherein said air bladder communicates with at least one air channel that passes through said main interface layer and is adapted for connection with a pressure source.

2. The interface device of claim 1, wherein said gasket has a height of between about 20 μm and about 30 μm.

3. The interface device of claim 1, wherein said gasket has a height of between about 23 μm and about 27 μm.

4. The interface device of claim 1, wherein said flexible lower surface of said at least one air bladder comprises a flexible diaphragm layer attached to the lower surface of said main interface layer.

5. The interface device of claim 1, wherein said flexible lower surface of said at least one air bladder comprises a thin layer of the rigid material forming the bulk of said main interface layer.

6. The interface device of claim 1, further comprising a waste reservoir in said main interface layer in fluid communication with said at least one outlet channel.

7. The interface device of claim 1, further comprising a microfluidic circuit comprising at least one of a mixing circuit, a branching structure, a reservoir, a valve, or a stop junction.

8. The interface device of claim 7, wherein said microfluidic circuit is in fluid communication between said inlet channel and said at least one interface channel.

9. The interface device of claim 7, wherein said microfluidic circuit is in fluid communication between said at least one interface channel and said outlet.

10. The interface device of claim 7, wherein said microfluidic circuit comprises at least one passive valve.

11. The interface device of claim 1, wherein said at least one interface channel is defined at least in part by an interface well or groove formed in said interface surface of said main interface layer.

12. The interface device of claim 1, wherein said gasket is formed from a resilient sheet material.

13. The interface device of claim 1, wherein said gasket is formed by application of said resilient material directly to said interface surface.

14. The interface device of claim 1, wherein said gasket is formed of an elastic material.

15. The interface device of claim 1, wherein said gasket is formed of a plastically deformable material.

16. The interface device of claim 1, wherein said gasket is formed of an adhesive material.

17. The interface device of claim 16, wherein said adhesive is adapted to adhere reversibly to said first surface of said substrate.

18. The interface device of claim 1, wherein said interface device is constructed from multiple layers, and wherein said interface device further comprises microfluidic circuit structures formed in at least two of said multiple layers.

19. A combination comprising the interface device of claim 1, and a microarray slide substrate bearing a biological sample.

20. The interface device of claim 1, wherein the gasket positioned at said interface surface has a plurality of openings formed therethrough, each said opening defining the perimeter of an interface channel or chamber connected to the inlet channel and the outlet channel.

21. The interface device of claim 20, further comprising a microfluidic branching structure in fluid communication between the said inlet channel and a plurality of said interface channels, said branching structure adapted to divide fluid entering said inlet among said plurality of interface channels.

22. The interface device of claim 20, further comprising a microfluidic circuit in fluid communication between at least two said interface channels and the said outlet channel, said microfluidic circuit adapted to combine fluids from said at least two interface channels into a single fluid stream flowing through said outlet channel.

23. The interface device of claim 20, wherein at least one said interface channel is defined at least in part by an interface well or groove formed in said interface surface of said main interface layer.

24. The interface device of claim 20, wherein said gasket is formed from a resilient sheet material.

25. The interface device of claim 20, wherein said gasket is formed of an elastic material.

26. The interface device of claim 20, wherein said gasket is formed of a plastically deformable material.

27. The interface device of claim 20, wherein said gasket is formed of an adhesive material.

28. The interface device of claim 27, wherein said adhesive is adapted to adhere reversibly to said first surface of said substrate.

29. The interface device of claim 20, wherein said interface device is formed of multiple layers, and wherein said interface device further comprises a 3D microfluidic circuit comprising microfluidic circuit components in at least two of said multiple layers.

30. The interface device of claim 29, wherein 3D microfluidic circuit comprises overlapping microfluidic circuit structures.

31. The interface device of claim 1 comprising two air bladders located at opposite ends of said interface channel, wherein said two air bladders are adapted to inflate and deflate reciprocally to produce agitation of fluid in said at least one interface channel.

* * * * *